(12) United States Patent
Nishio et al.

(10) Patent No.: US 10,076,644 B2
(45) Date of Patent: Sep. 18, 2018

(54) METHOD AND APPARATUS FOR TREATING URETHRAL STRICTURE

(71) Applicant: TERUMO KABUSHIKI KAISHA, Shibuya-ku (JP)

(72) Inventors: Kosuke Nishio, Machida (JP); Riyaheh Arastoo, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 25 days.

(21) Appl. No.: 14/584,152

(22) Filed: Dec. 29, 2014

(65) Prior Publication Data

US 2015/0327982 A1 Nov. 19, 2015

Related U.S. Application Data

(63) Continuation-in-part of application No. 14/451,784, filed on Aug. 5, 2014.
(Continued)

(51) Int. Cl.
| | |
|---|---|
| *A61M 29/00* | (2006.01) |
| *A61M 25/10* | (2013.01) |
| *A61F 2/958* | (2013.01) |
| *A61F 2/04* | (2013.01) |
| *A61M 25/00* | (2006.01) |
| *A61M 25/01* | (2006.01) |

(52) U.S. Cl.
CPC ........ *A61M 29/00* (2013.01); *A61M 25/0068* (2013.01); *A61M 25/10* (2013.01); *A61F 2/04* (2013.01); *A61F 2/958* (2013.01); *A61F 2002/047* (2013.01); *A61F 2230/0069* (2013.01); *A61M 2025/0175* (2013.01)

(58) Field of Classification Search
USPC ...................................................... 623/1.23
See application file for complete search history.

(56) References Cited

U.S. PATENT DOCUMENTS

| | | |
|---|---|---|
| 4,771,773 A | 9/1988 | Kropf |
| 5,108,416 A | 4/1992 | Ryan et al. |

(Continued)

FOREIGN PATENT DOCUMENTS

| | | |
|---|---|---|
| WO | 97/10871 A1 | 3/1997 |
| WO | 01/67991 A1 | 9/2001 |

(Continued)

OTHER PUBLICATIONS

"Suction Cup Tape", Suction Cup Tape, N.p., Jul. 23, 2012. Web. Jan. 6, 2016. <http://www.inventables.com/technologies/suction-cup-tape> (7 pages).

(Continued)

*Primary Examiner* — Leslie Lopez
(74) *Attorney, Agent, or Firm* — Buchanan Ingersoll & Rooney PC

(57) ABSTRACT

A method of treating a treatment area of a body lumen includes inserting an elongated member into the body lumen, wherein the elongated member is configured to guide a delivery member, the delivery member possessing an outer portion with a treatment part, moving the delivery member to the treatment area, applying the treatment part to the treatment area, and withdrawing the delivery member from the treatment area.

21 Claims, 36 Drawing Sheets

Related U.S. Application Data

(60) Provisional application No. 61/994,499, filed on May 16, 2014.

(56) References Cited

U.S. PATENT DOCUMENTS

| | | | | |
|---|---|---|---|---|
| 5,197,978 | A | * | 3/1993 | Hess .................... A61F 2/82 606/194 |
| 5,779,732 | A | | 7/1998 | Amundson |
| 5,902,228 | A | | 5/1999 | Schulsinger et al. |
| 5,957,929 | A | | 9/1999 | Brenneman |
| 6,475,232 | B1 | | 11/2002 | Babbs et al. |
| 6,506,180 | B1 | | 1/2003 | Lary |
| 6,939,381 | B2 | | 9/2005 | Stark et al. |
| 7,559,953 | B2 | | 7/2009 | Sarac |
| 7,771,463 | B2 | | 8/2010 | Ton et al. |
| 7,862,542 | B1 | * | 1/2011 | Harmon, Sr. ...... A61B 1/00135 600/115 |
| 2003/0149489 | A1 | * | 8/2003 | Stark .................... A61F 2/04 623/23.66 |
| 2006/0047336 | A1 | | 3/2006 | Gale et al. |
| 2006/0079957 | A1 | * | 4/2006 | Chin .................... A61F 2/06 623/1.23 |
| 2006/0211973 | A1 | | 9/2006 | Gregory et al. |
| 2007/0088431 | A1 | | 4/2007 | Bourang et al. |
| 2008/0065011 | A1 | | 3/2008 | Marchand et al. |
| 2011/0307052 | A1 | | 12/2011 | Bourang et al. |
| 2013/0013083 | A1 | * | 1/2013 | Blum .................... A61F 2/06 623/23.7 |
| 2015/0209557 | A1 | * | 7/2015 | Tal ................... A61B 17/12109 600/435 |

FOREIGN PATENT DOCUMENTS

| | | |
|---|---|---|
| WO | 03/050266 A2 | 6/2003 |
| WO | 2005/077433 A1 | 8/2005 |
| WO | 2009/059217 A2 | 5/2009 |
| WO | 2013/137977 A1 | 9/2013 |

OTHER PUBLICATIONS

Communication and Search Report dated Jan. 20, 2016 issued in the corresponding European Patent Application No. 15179250.4-1654 (11 pages).

* cited by examiner

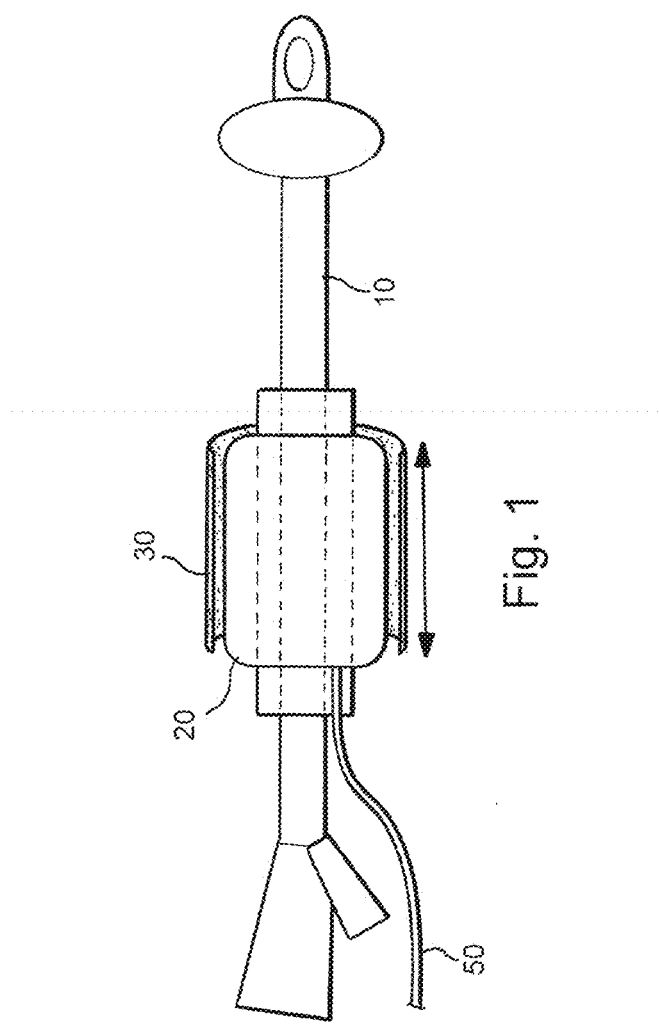

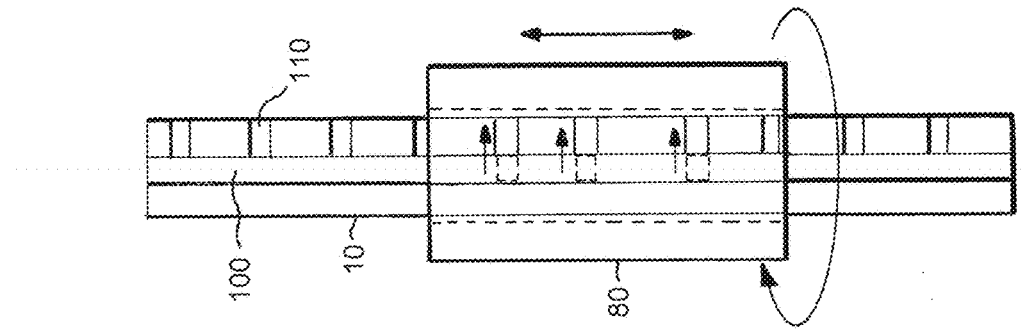
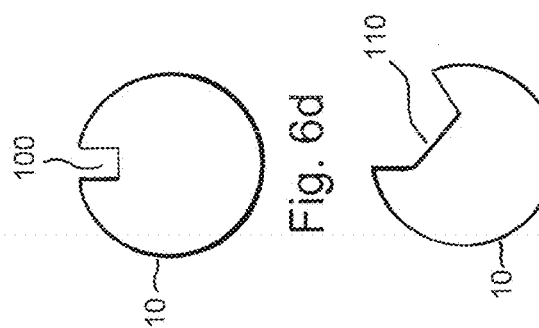
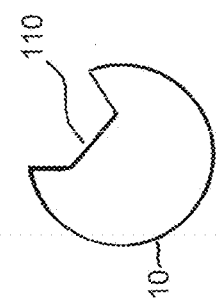
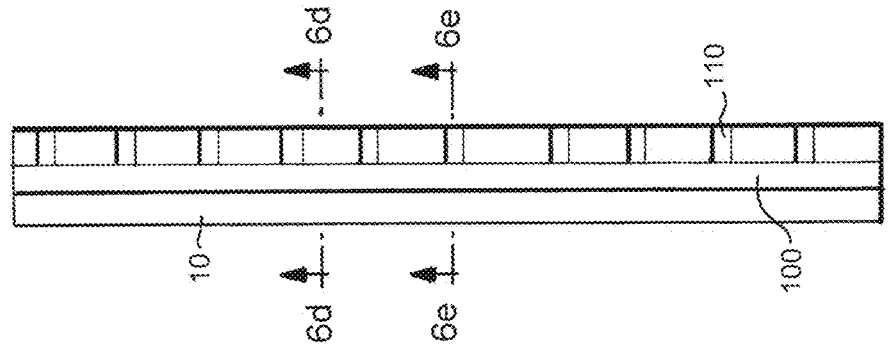
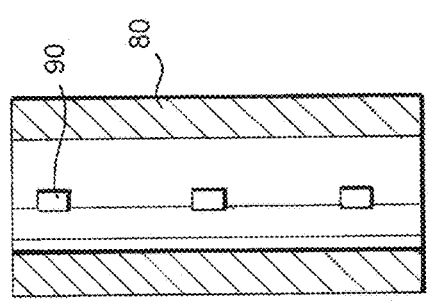
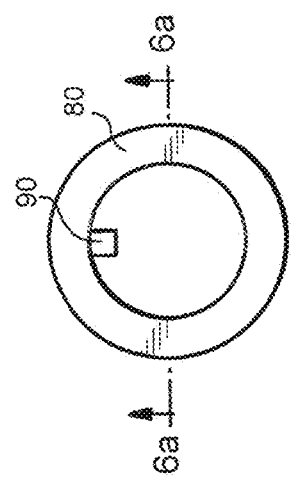

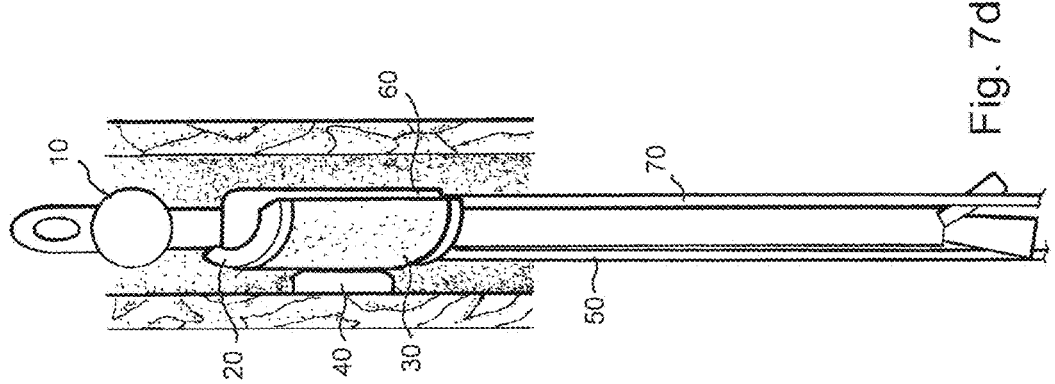
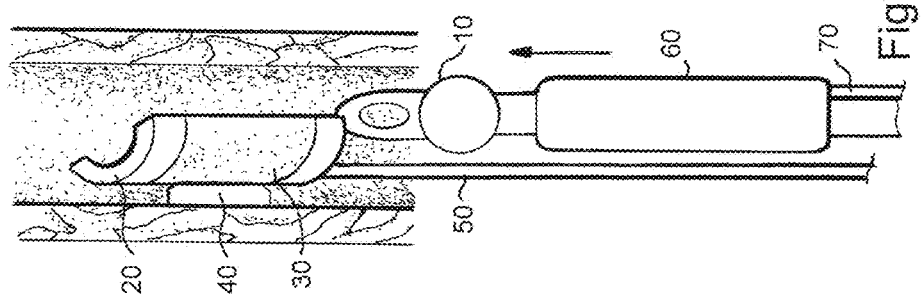
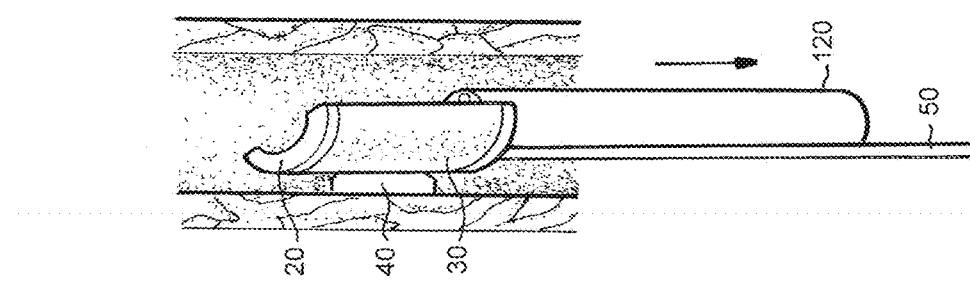
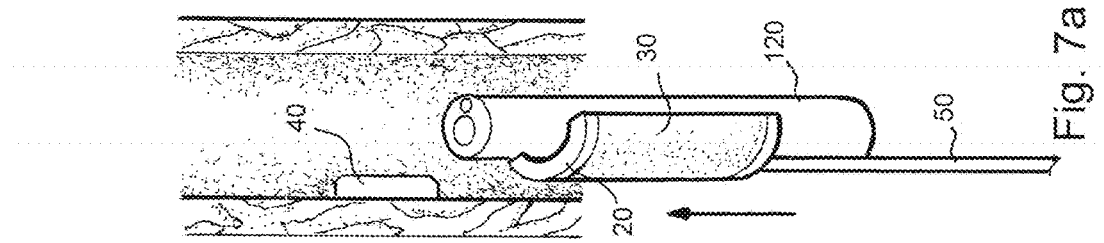

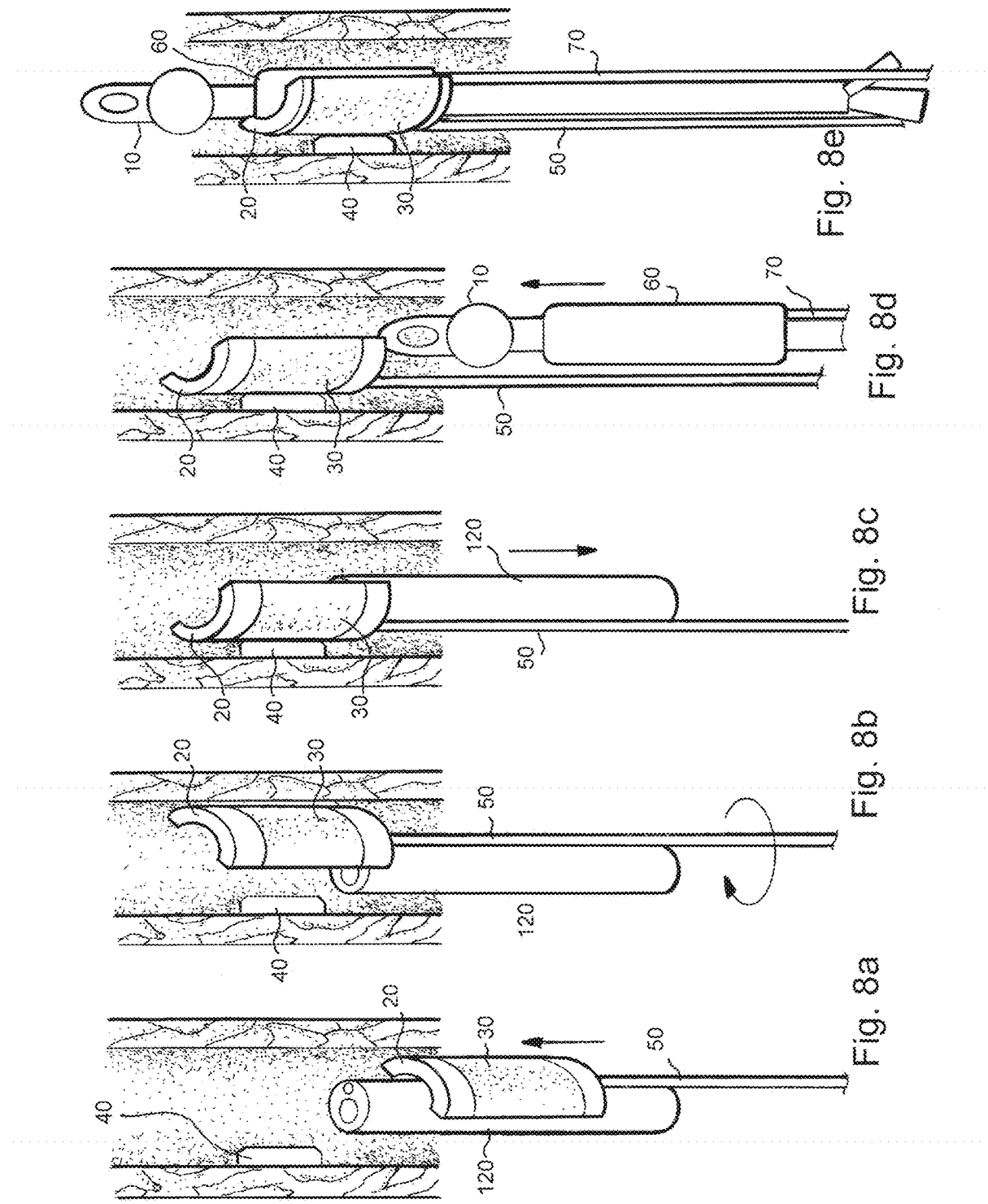

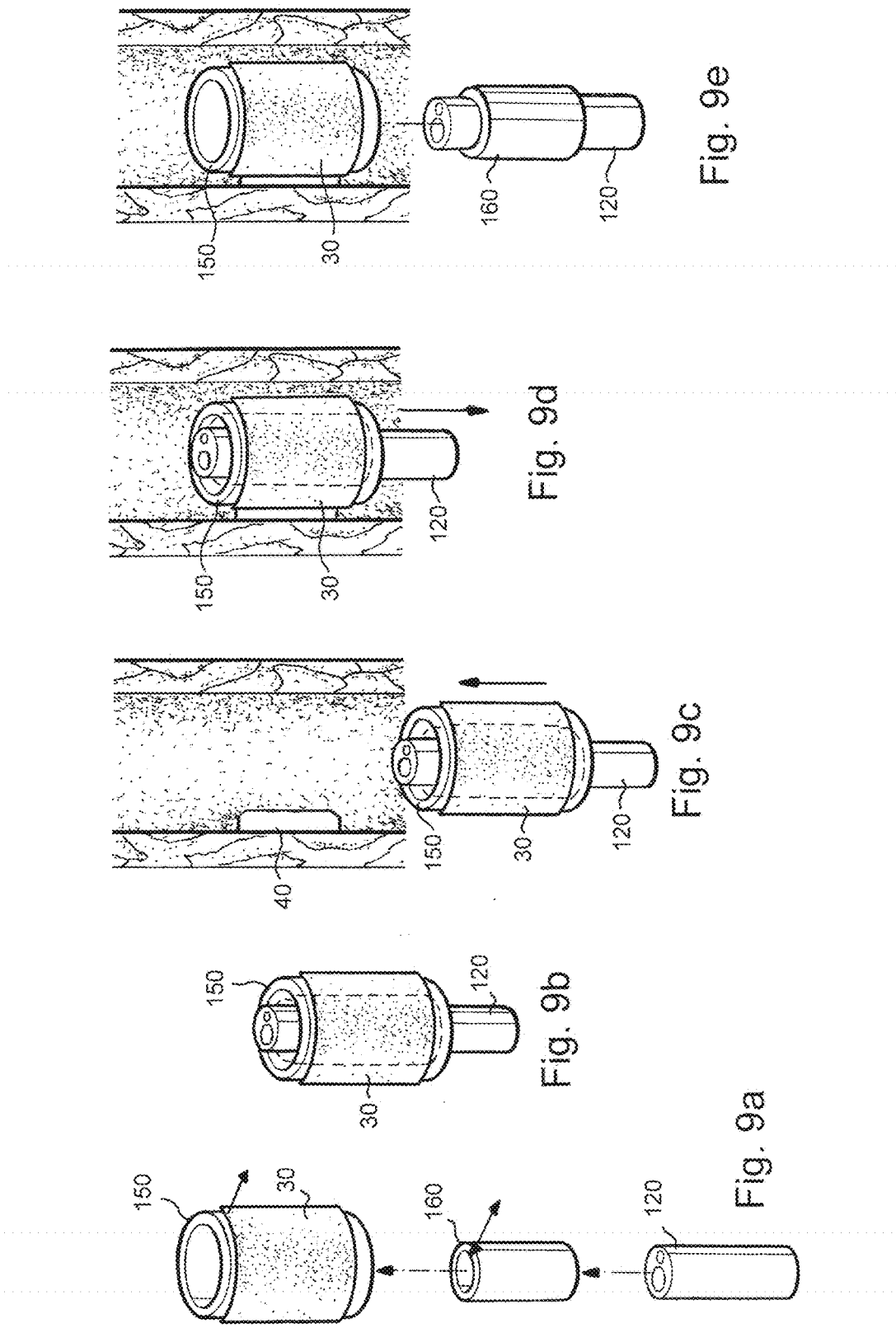

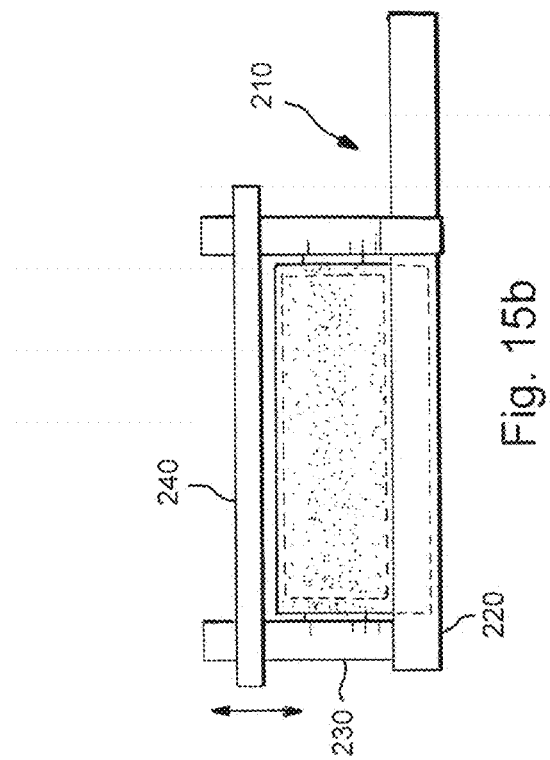
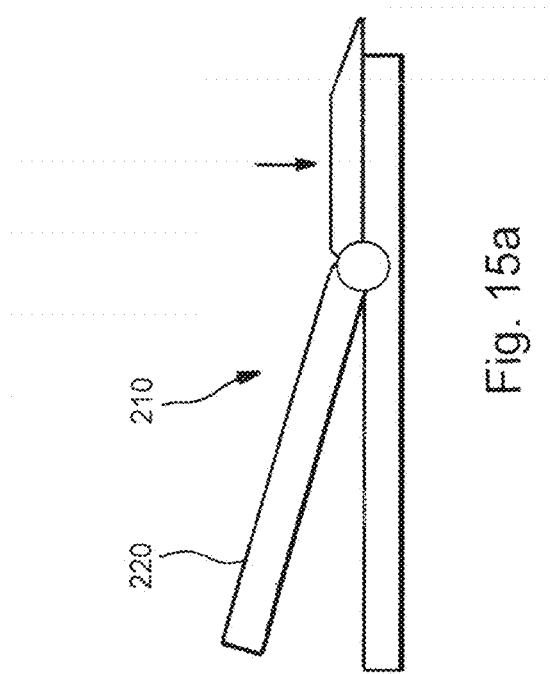

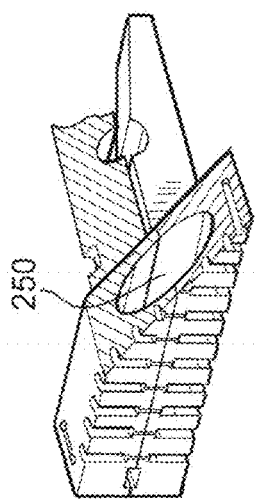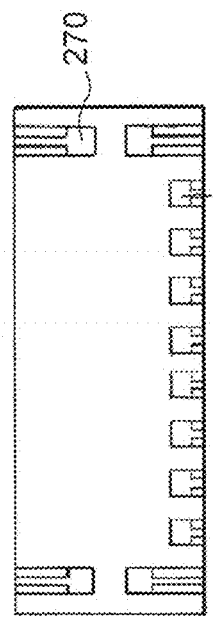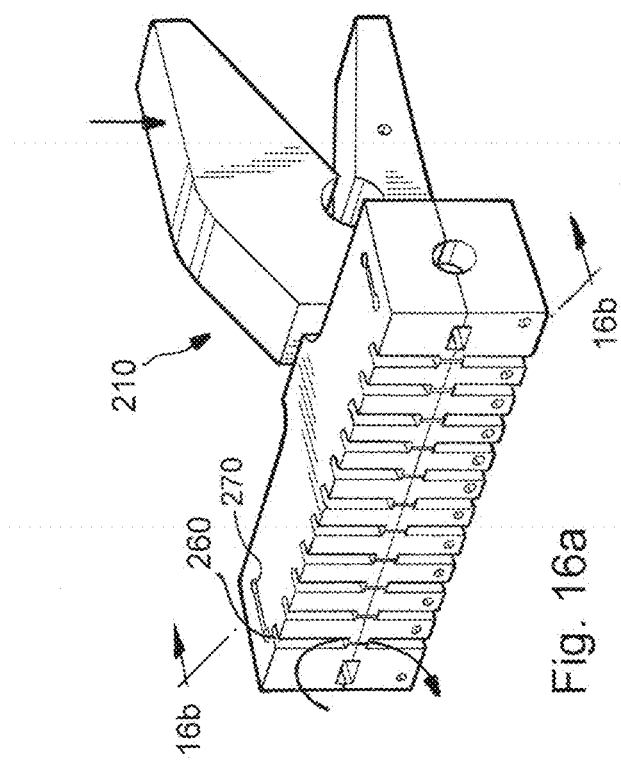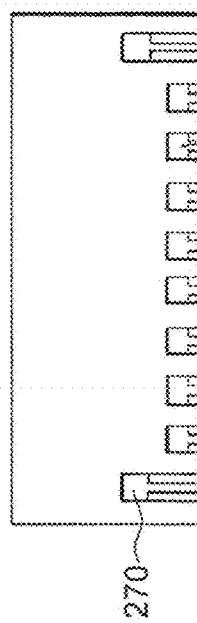

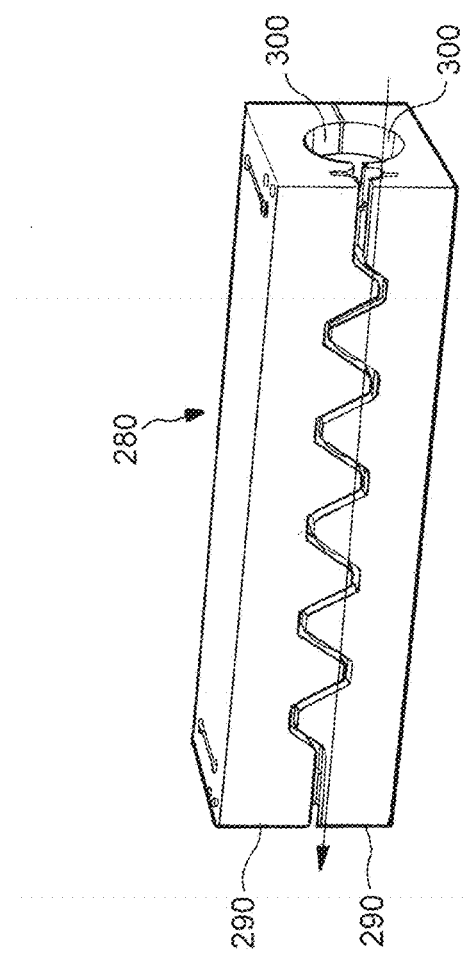
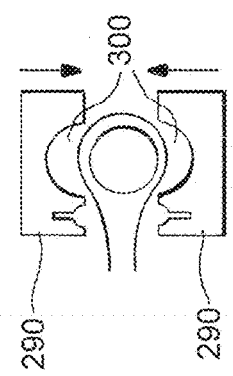
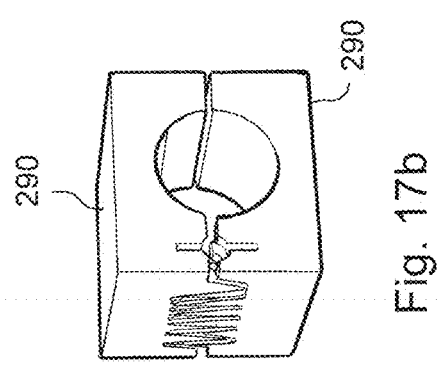
Fig. 17a
Fig. 17b
Fig. 17c

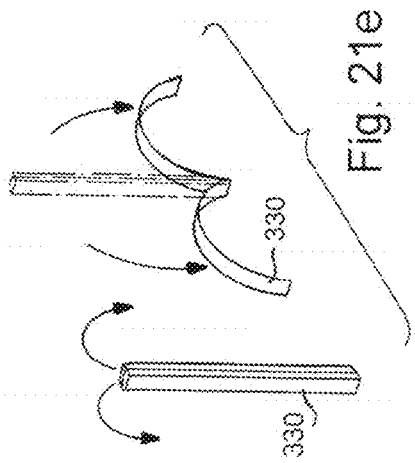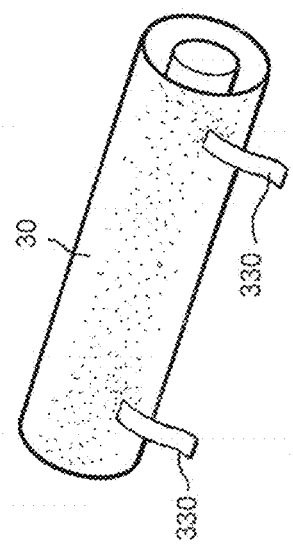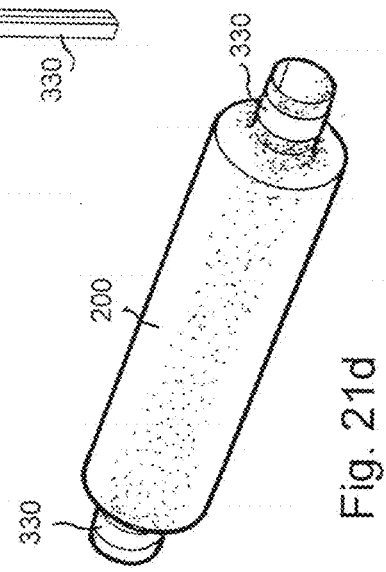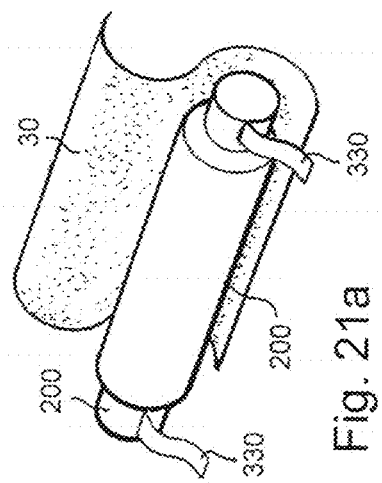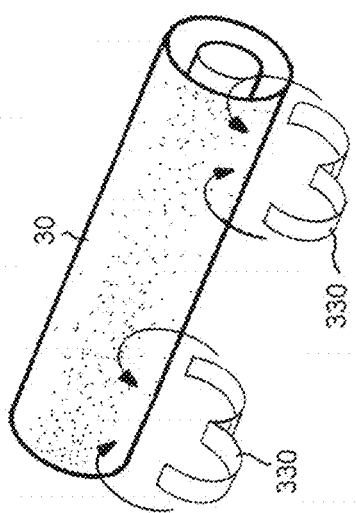

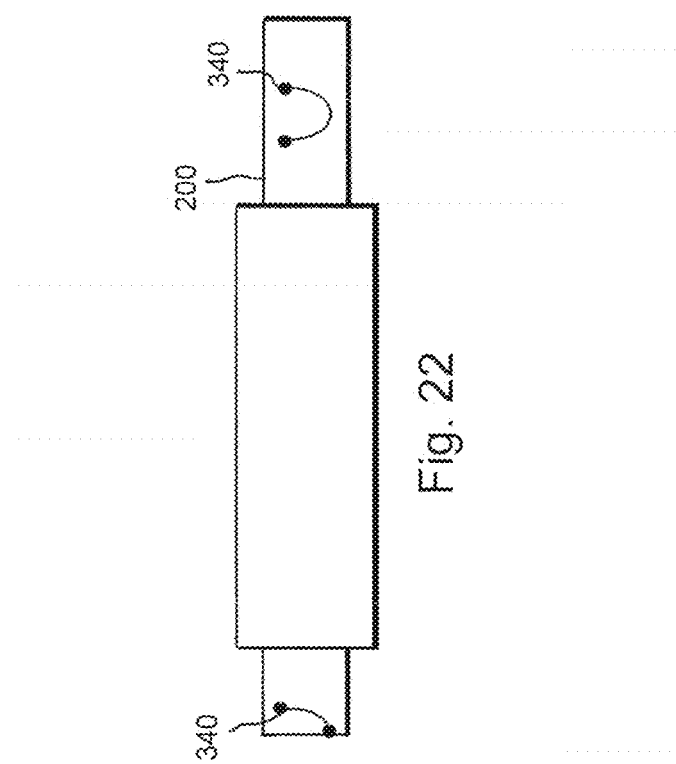

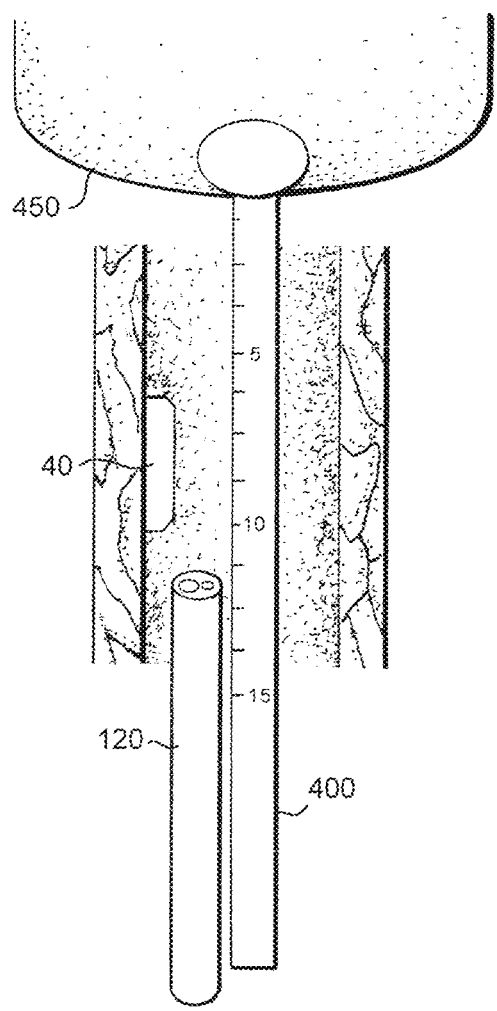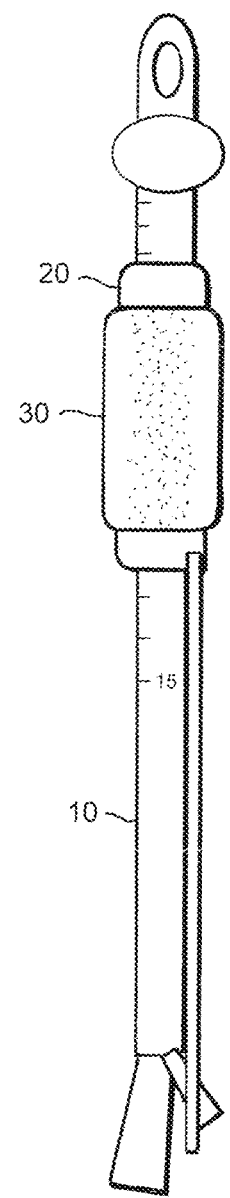
Fig. 24 a
Fig. 24b

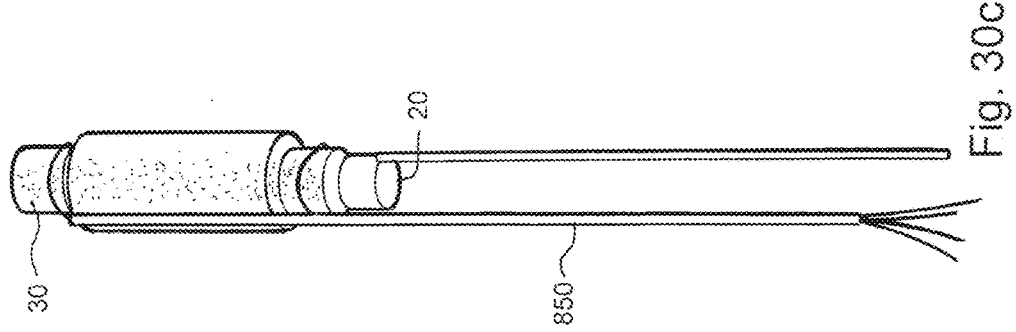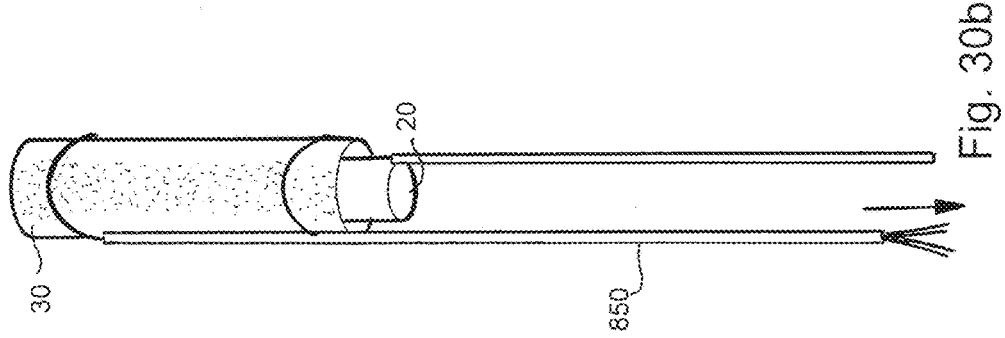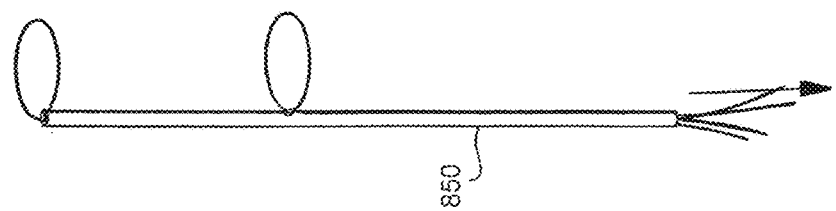

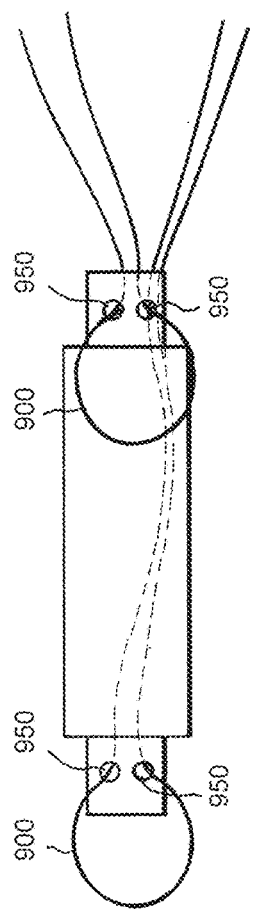
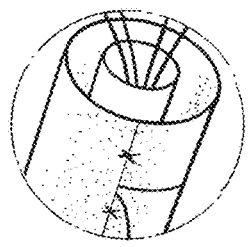
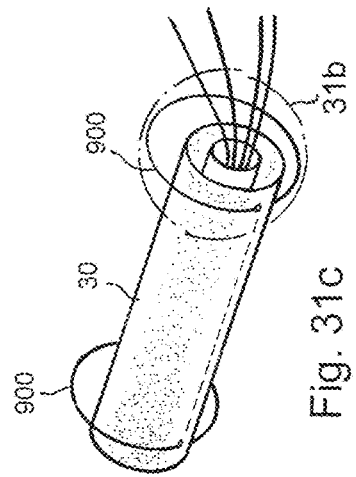
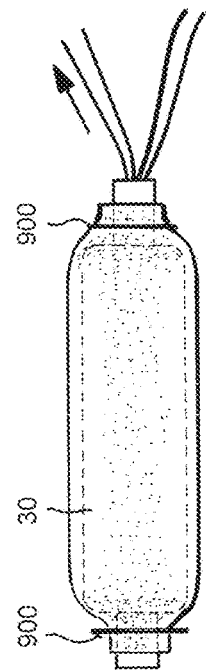
Fig. 31a
Fig. 31b
Fig. 31c
Fig. 31d

METHOD AND APPARATUS FOR TREATING URETHRAL STRICTURE

CROSS-REFERENCE TO RELATED APPLICATIONS

The present application is a continuation-in-part application of U.S. patent application Ser. No. 14/451,784 filed on Aug. 5, 2014, and claims the benefit under 35 U.S.C. § 119(e) to U.S. Provisional Application No. 61/994,499 filed on May 16, 2014, the entire content of each of which is incorporated by reference herein.

TECHNOLOGICAL FIELD

The disclosure here pertains generally to a method and apparatus for treating urethral stricture. More particularly, the disclosure is directed to a trans-urethral urethroplasty method and apparatus.

BACKGROUND DISCUSSION

Known treatment options for urethral stricture, which is an abnormal narrowing of the urethra, include urethroplasty surgery as well as minimally invasive procedures such as dilation, stent implantation, and urethrotomy. Due to the invasiveness of urethroplasty surgery, it is only recommended in extreme cases of urethral stricture. However, minimally invasive procedures currently in use to treat urethral stricture can be of limited long-term effectiveness because they do not promote epithelial function at the treatment site. Accordingly, a need exists for a practical, minimally invasive treatment of urethral stricture which promotes epithelial function at the treatment site.

SUMMARY

One aspect of the disclosure here involves a method of treating a treatment area of a body lumen, the method including inserting an elongated member into the body lumen, wherein the elongated member is configured to guide a delivery member, the delivery member possessing an outer portion having a treatment part, moving the delivery member to the treatment area, applying the treatment part to the treatment area, and withdrawing the delivery member from the treatment area.

An active component of the treatment part can be selected from one or more of a drug, a cultured cell and harvested tissue. In embodiments in which the treatment part includes a drug, one or more of a collagen inhibitor such as mithramycine, mitomicyn-c, tranilast, halofuginone, or any analogs thereof, an anti-inflammatory agent such as steroids, colchicine, NSAIDs, or any analogs thereof, an anti-cancer agent such as MMC, taxotere, or any analogs thereof, an immunosuppressive agent such as sirolimus, evelolimus, zotalolimus, biolimus, or any analogs thereof, and/or a cell growth enhancing constituent such as EGF, PRP, or any analogs thereof, can be used. Furthermore, in embodiments in which the treatment part includes a biological material, cultured cell and harvested tissue from, for example, buccal mucosa, bladder mucosa, intestinal mucosa, penile skin and/or thigh skin could be selected. A form of the treatment part, which is composed of one or more of a drug/cultured cell/harvested tissue on the delivery member, could be a liquid/gel coating, powder form, film shape, or membrane form. For a membrane form, a mesh-like structure could be used.

Another aspect of the disclosure involves, when a treatment part in membrane form (i.e., a treatment membrane) is selected, a method of mounting the treatment membrane to a delivery member, the method including wrapping the treatment membrane around the delivery member, pinching opposite overlapped edges of the treatment membrane together, and attaching the opposite overlapped edges of the treatment membrane together.

A further aspect of the disclosure involves a method of delivering a therapeutic device to a treatment area of a body lumen, the therapeutic device including a) a delivery member possessing at least one attachment part and b) a treatment membrane, the method including wrapping the treatment membrane on the delivery member, attaching the treatment membrane to the attachment part of the delivery member, and moving the delivery member toward the treatment area.

An additional aspect of the disclosure involves a method of delivering a therapeutic device to a treatment area of a body lumen, the therapeutic device including a) a delivery member and b) a treatment membrane attached to the delivery member, the method including wrapping the treatment membrane on the delivery member, moving the delivery member toward the treatment area, detaching the treatment membrane from the delivery member, and withdrawing the delivery member from the body lumen.

BRIEF DESCRIPTION OF THE DRAWING FIGURES

Additional features and aspects of the method and apparatus for treating urethral stricture disclosed here will become more apparent from the following detailed description considered with reference to the accompanying drawing figures in which like elements are designated by like reference numerals.

FIG. 1 is a longitudinal schematic view of an apparatus for delivering a treatment part to a treatment area.

FIG. 2a illustrates a view of a first step of the procedure, and FIG. 2b illustrates a view of a second step of the procedure.

FIG. 3a illustrates a view of a first step of the procedure, FIG. 3b illustrates a view of a second step of the procedure, and FIG. 3c illustrates a view of a third step of the procedure.

FIG. 4a illustrates a view of a first step of the procedure, FIG. 4b illustrates a view of a second step of the procedure, and FIG. 4c illustrates a view of a third step of the procedure.

Figures 4A, 4B, 4C:
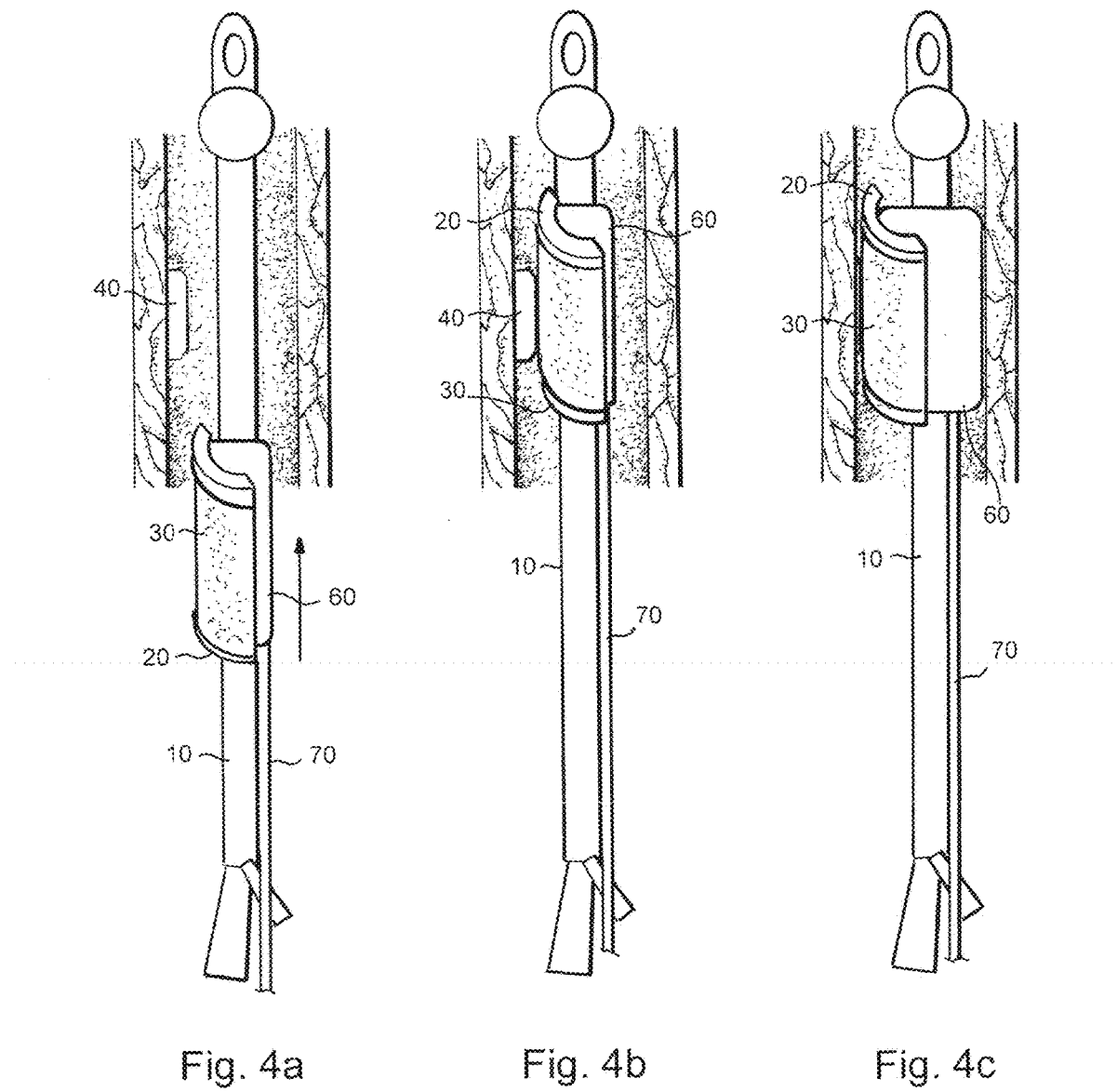
FIGS. 4a-4c illustrate partially sectional views of an exemplary delivery procedure using an apparatus for delivering a treatment part to a treatment area.
Figure 5D:
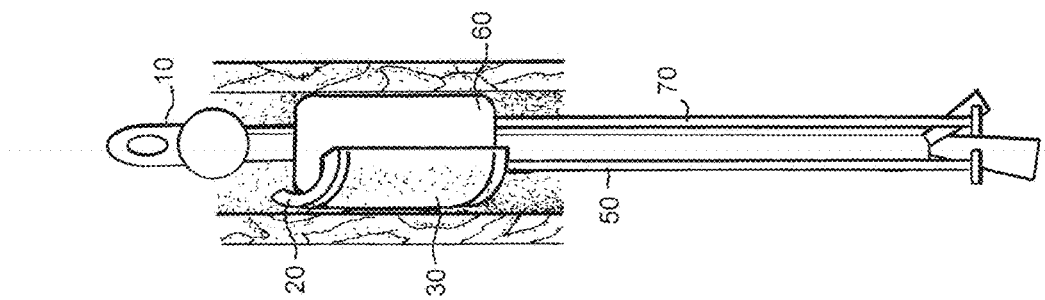
Figure 5C:
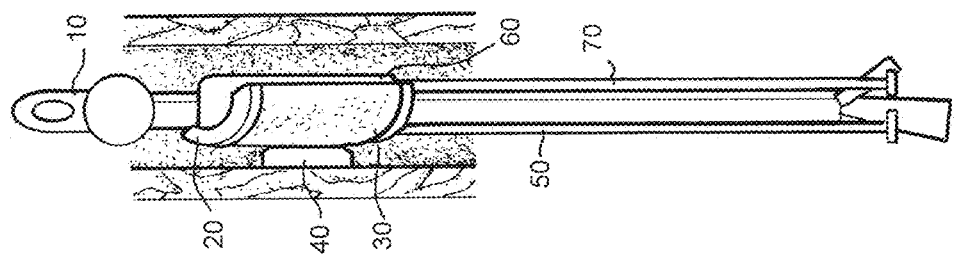
Figure 5B:
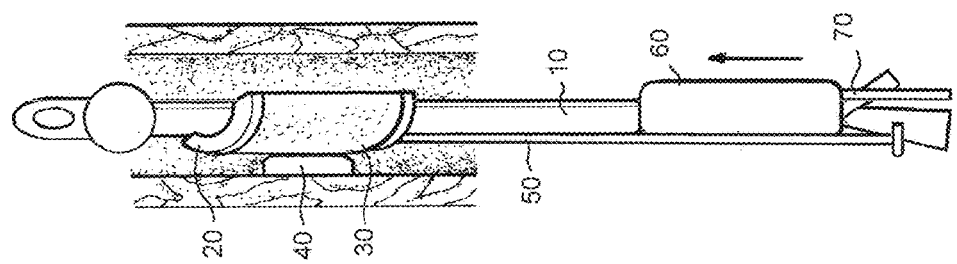
Figure 5A:
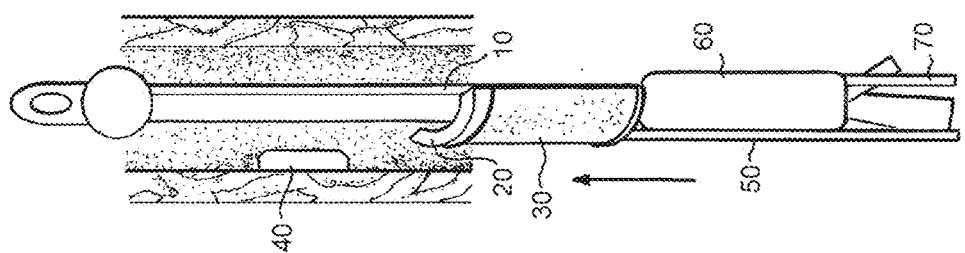

FIGS. 5a-5d illustrate partially sectional views of an exemplary delivery procedure using the apparatus of FIGS. 4a-4c for delivering a treatment part to a treatment area. FIG. 5a illustrates a view of a first step of the procedure, FIG. 5b illustrates a view of a second step of the procedure, FIG. 5c illustrates a view of a third step of the procedure, and FIG. 5d illustrates a fourth step of the procedure.

FIGS. 6a-6f illustrate cross-sectional views of an exemplary delivery procedure using an apparatus for delivering a treatment part to a treatment area. FIG. 6a illustrates a longitudinal cross-sectional view of a delivery member used in the procedure, FIG. 6b illustrates an axial cross-sectional view of a delivery member used in the procedure, FIG. 6c illustrates a longitudinal cross-sectional view of an elongated member used in the procedure, FIG. 6d illustrates an axial cross-sectional view taken along line 6*d* of FIG. 6*c*, FIG. 6*e* illustrates an axial cross-sectional view taken along line 6*e* of FIG. 6*c*, and FIG. 6*f* illustrates a view of a step of the procedure.

FIGS. 7*a*-7*d* illustrate partially sectional views of an exemplary delivery procedure using an apparatus for delivering a treatment part to a treatment area. FIG. 7*a* illustrates a view of a first step of the procedure, FIG. 7*b* illustrates a view of a second step of the procedure, FIG. 7*c* illustrates a view of a third step of the procedure, and FIG. 7*d* illustrates a view of a fourth step of the procedure.

FIGS. 8*a*-8*e* illustrate partially sectional views of an exemplary delivery procedure using the apparatus of FIGS. 7*a*-7*d* for delivering a treatment part to a treatment area. FIG. 8*a* illustrates a view of a first step of the procedure, FIG. 8*b* illustrates a view of a second step of the procedure, FIG. 8*c* illustrates a view of a third step of the procedure, FIG. 8*d* illustrates a view of a fourth step of the procedure, and FIG. 8*e* illustrates a view of a fifth step of the procedure.

FIGS. 9*a*-9*e* illustrate partially sectional views of an exemplary delivery procedure using an apparatus for delivering a treatment part to a treatment area. FIG. 9*a* illustrates a view of a first step of the procedure, FIG. 9*b* illustrates a view of a second step of the procedure, FIG. 9*c* illustrates a view of a third step of the procedure, FIG. 9*d* illustrates a view of a fourth step of the procedure, and FIG. 9*e* illustrates a view of a fifth step of the procedure.

Figure 10E:
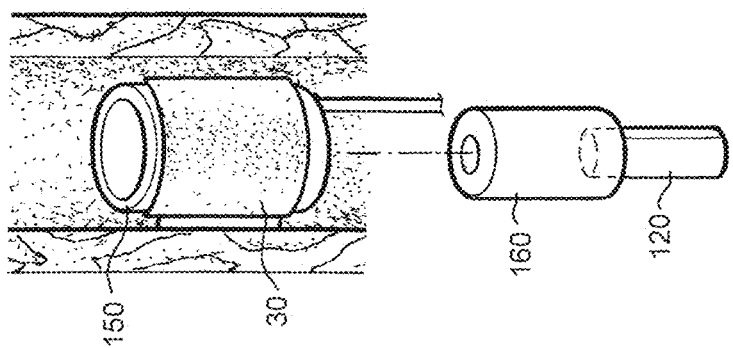
Figure 10D:
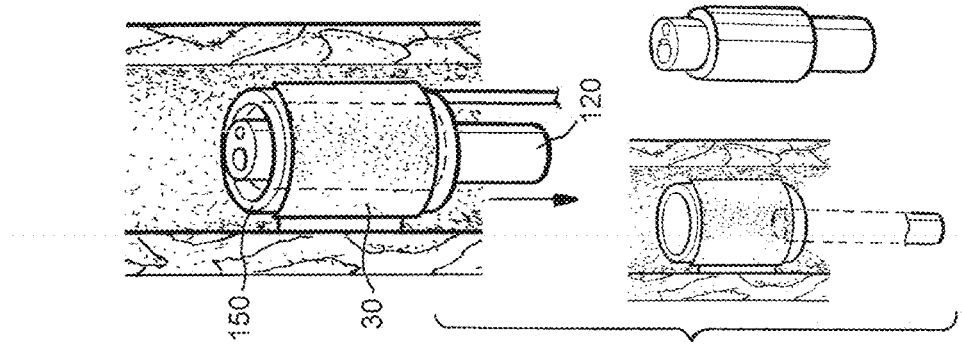
Figure 10C:
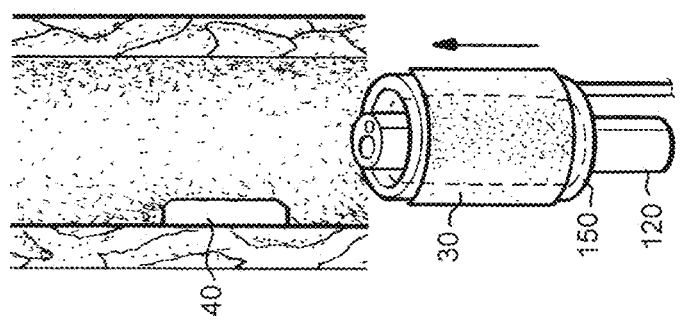
Figure 10B:
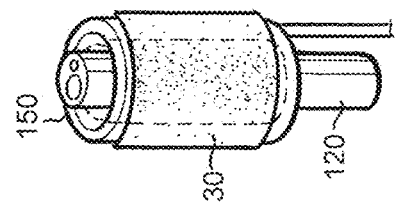
Figure 10A:
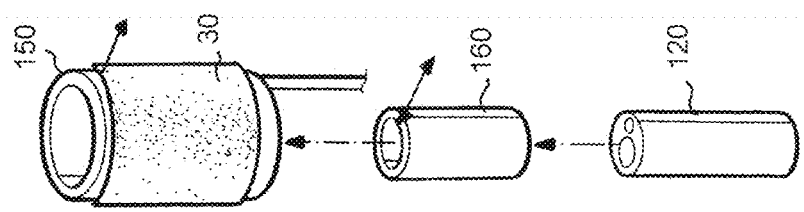

FIGS. 10*a*-10*e* illustrate partially sectional views of an exemplary delivery procedure using an apparatus for delivering a treatment part to a treatment area. FIG. 10*a* illustrates a view of a first step of the procedure, FIG. 10*b* illustrates a view of a second step of the procedure, FIG. 10*c* illustrates a view of a third step of the procedure, FIG. 10*d* illustrates a view of a fourth step of the procedure, and FIG. 10*e* illustrates a view of a fifth step of the procedure.

Figure 11E:
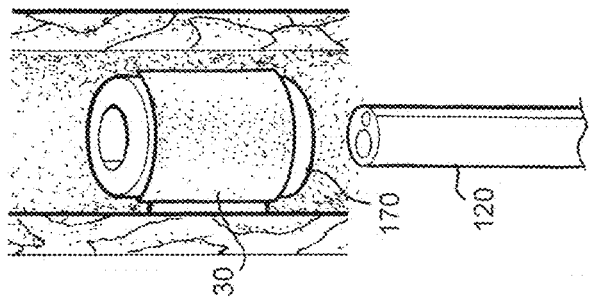
Figure 11D:
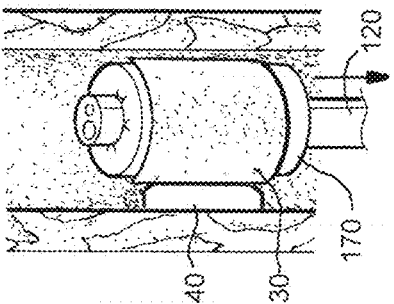
Figure 11C:
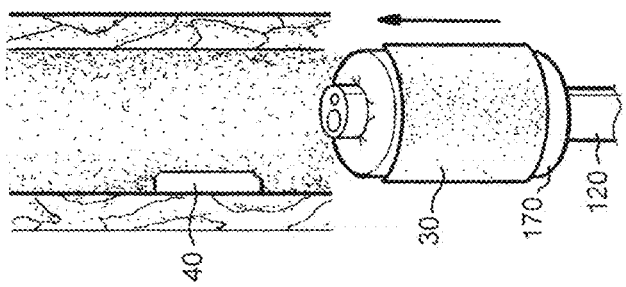
Figure 11B:
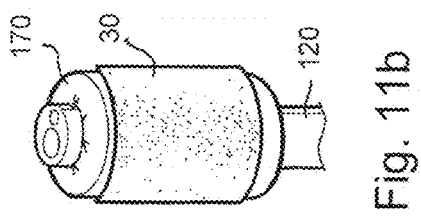
Figure 11A:
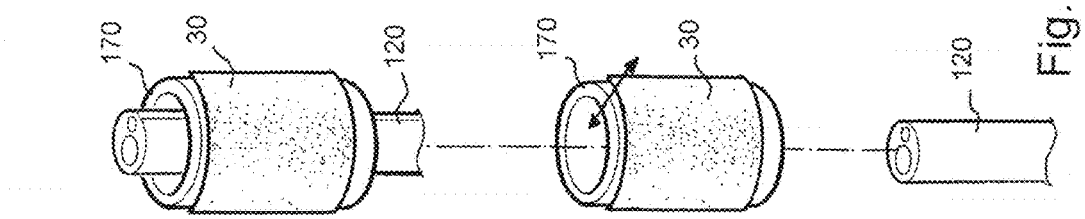

FIGS. 11*a*-11*e* illustrate partially sectional views of an exemplary delivery procedure using an apparatus for delivering a treatment part to a treatment area. FIG. 11*a* illustrates a view of a first step of the procedure, FIG. 11*b* illustrates a view of a second step of the procedure, FIG. 11*c* illustrates a view of a third step of the procedure, FIG. 11*d* illustrates a view of a fourth step of the procedure, and FIG. 11*e* illustrates a view of a fifth step of the procedure.

Figure 12E:
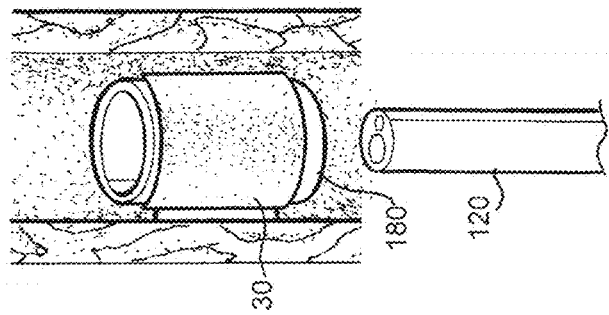
Figure 12D:
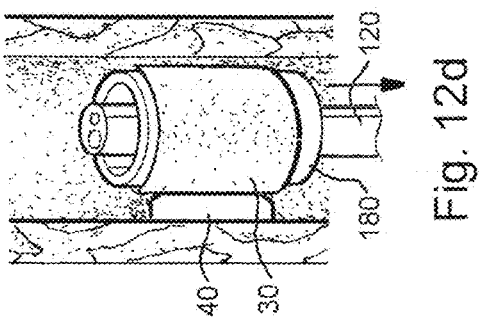
Figure 12C:
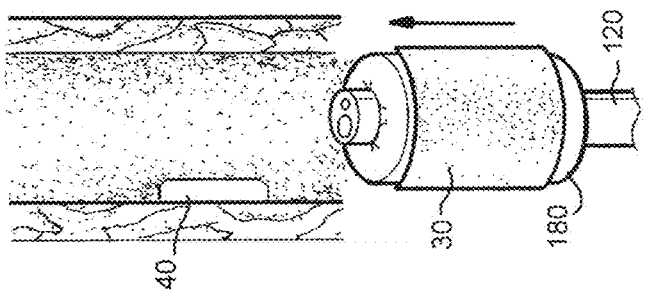
Figure 12B:
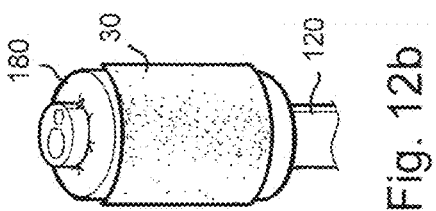
Figure 12A:
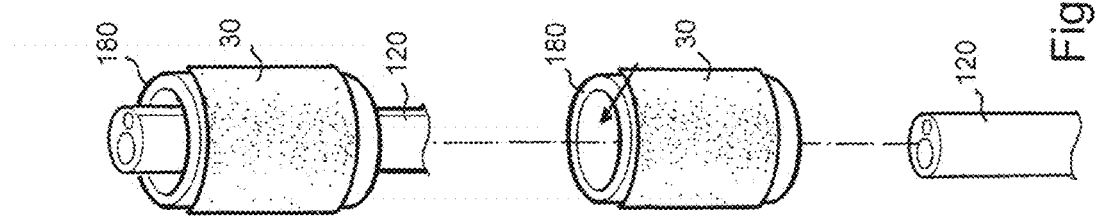

FIGS. 12*a*-12*e* illustrate partially sectional views of an exemplary delivery procedure using an apparatus for delivering a treatment part to a treatment area. FIG. 12*a* illustrates a view of a first step of the procedure, FIG. 12*b* illustrates a view of a second step of the procedure, FIG. 12*c* illustrates a view of a third step of the procedure, FIG. 12*d* illustrates a view of a fourth step of the procedure, and FIG. 12*e* illustrates a view of a fifth step of the procedure.

Figure 13B:
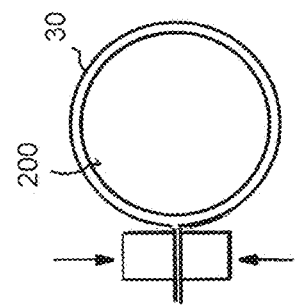
Figure 13D:
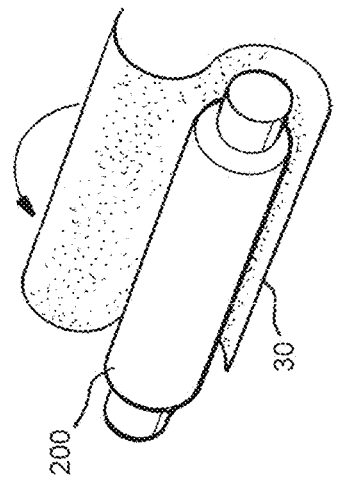
Figure 13A:
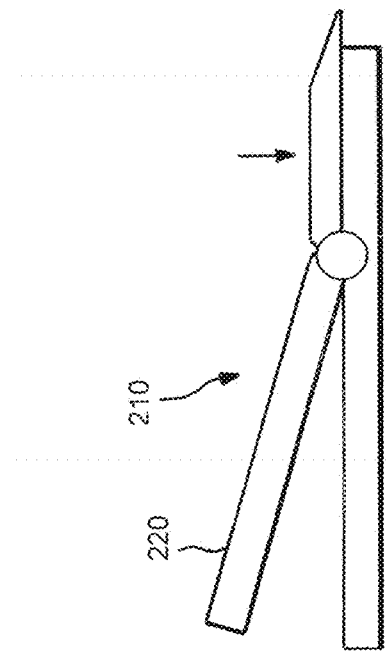
Figure 13C:
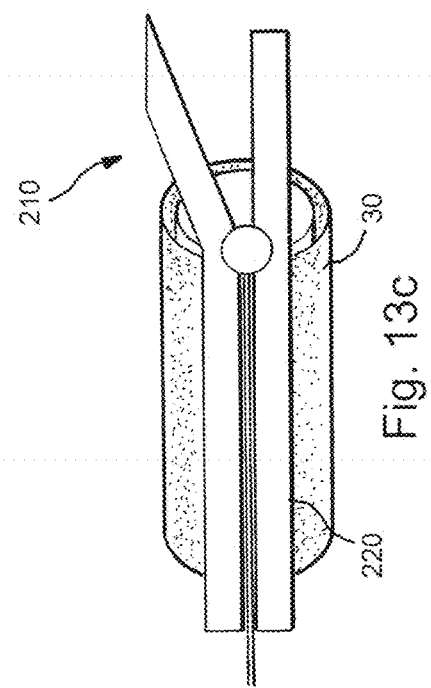
Figure 13F:
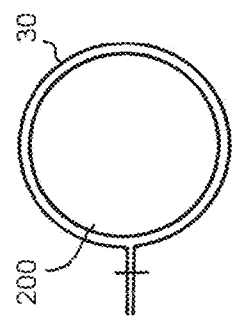
Figure 13E:
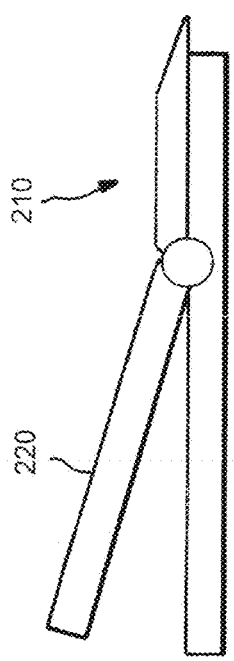

FIGS. 13*a*-13*f* illustrate various views of an exemplary mounting procedure using an apparatus for mounting a treatment membrane to a delivery member. FIG. 13*a* illustrates a perspective view of a first step of the procedure, FIG. 13*b* illustrates a perspective view of second step of the procedure, FIG. 13*c* illustrates a perspective view of a third step of the procedure, FIG. 13*d* illustrates an axial cross-sectional view of the third step of the procedure, FIG. 13*e* illustrates a perspective view of a fourth step of the procedure, and FIG. 13*f* illustrates an axial cross-sectional view of the fourth step of the procedure.

Figure 14B:
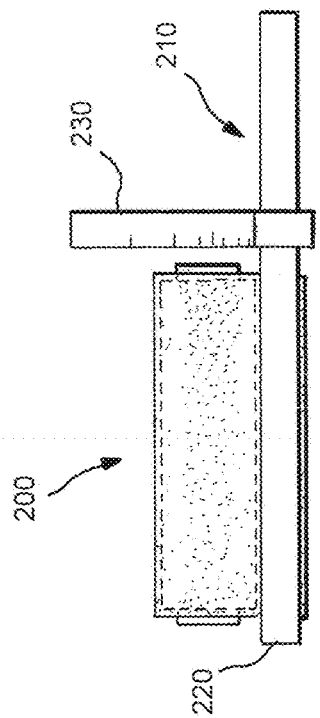
Figure 14A:
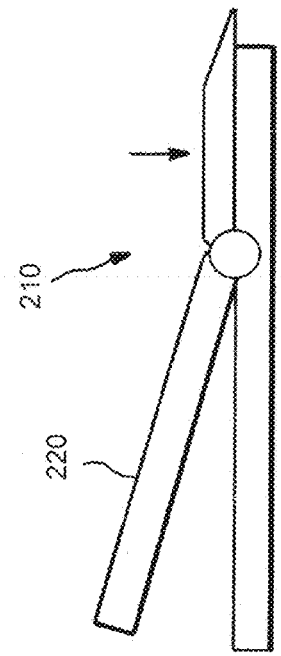

FIGS. 14*a* and 14*b* illustrate various views of an exemplary mounting procedure using an apparatus for mounting a treatment membrane to a delivery member. FIG. 14*a* illustrates a view of a first step of the procedure, and FIG. 14*b* illustrates a view of a second step of the procedure.

FIGS. 15*a* and 15*b* illustrate various views of an exemplary mounting procedure using an apparatus for mounting a treatment membrane to a delivery member. FIG. 15*a* illustrates a view of a first step of the procedure, and FIG. 15*b* illustrates a view of a second step of the procedure.

FIGS. 16*a*-16*d* illustrate various views of an exemplary mounting procedure using an apparatus for mounting a treatment membrane to a delivery member. FIG. 16*a* illustrates a perspective view of the procedure, FIG. 16*b* illustrates a cutaway view along line 16*b* of FIG. 16*a*, FIG. 16*c* illustrates bottom view of the procedure, and FIG. 16*d* illustrates a top view of the procedure.

FIGS. 17*a*-17*c* illustrate various views of an exemplary mounting procedure using an apparatus for mounting a treatment membrane to a delivery member. FIG. 17*a* illustrates a first perspective view of the procedure, FIG. 17*b* illustrates a second perspective view of the procedure, and FIG. 17*c* illustrates a side view of the procedure.

Figure 18A:
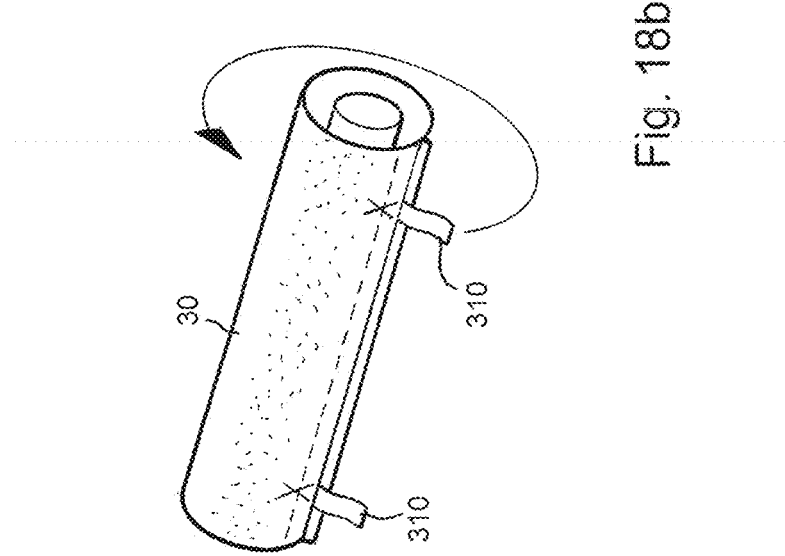
Figure 18B:
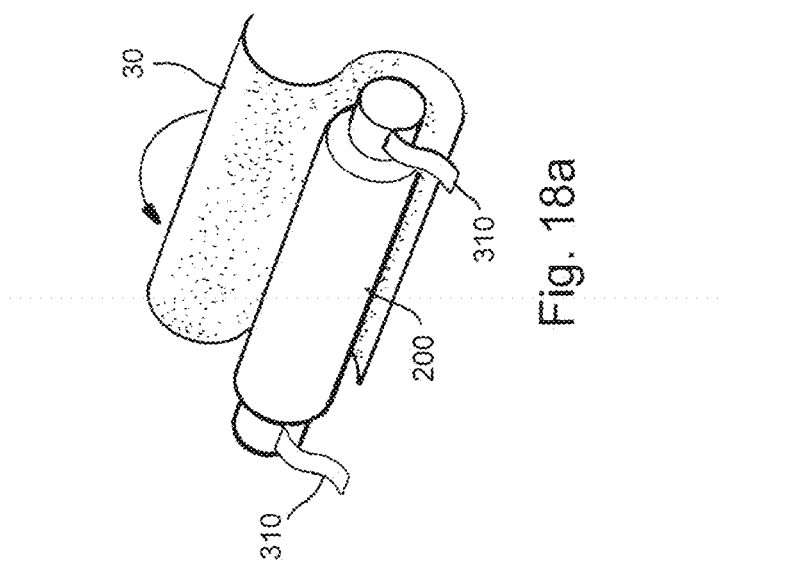

FIGS. 18*a* and 18*b* illustrate perspective views of an exemplary attaching procedure using an attachment part of a delivery member. FIG. 18*a* illustrates a view of a first step of the procedure, and FIG. 18*b* illustrates a view of a second step of the procedure.

Figure 19C:
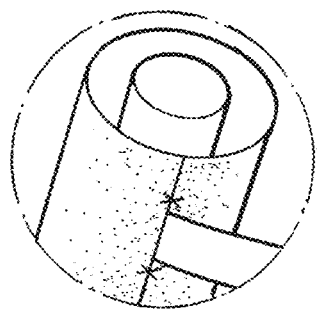
Figure 19B:
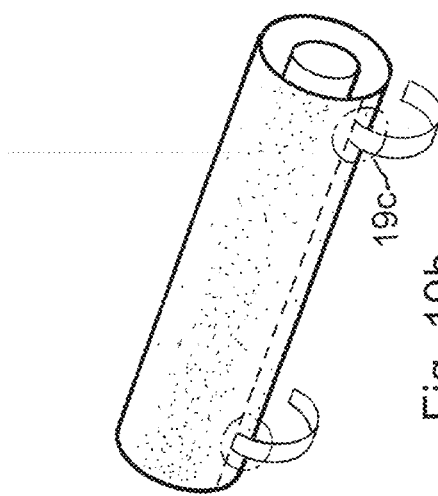
Figure 19A:
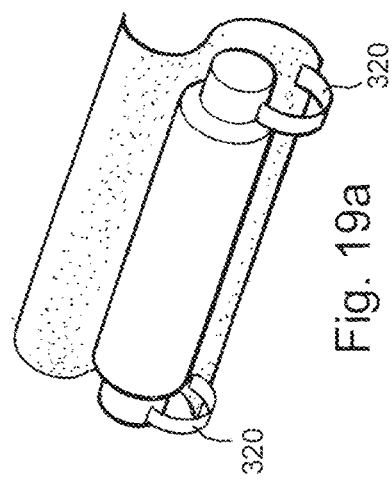
Figure 19D:
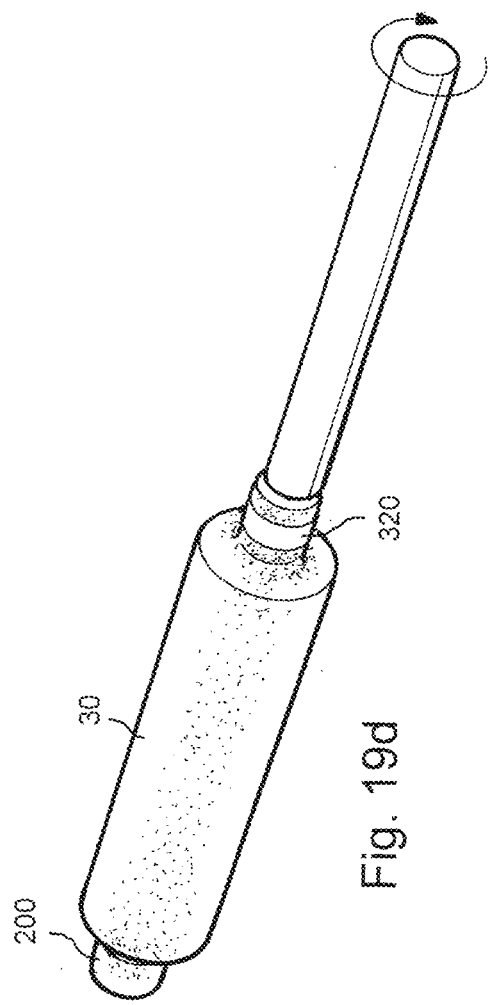

FIGS. 19*a*-19*d* illustrate perspective views of an exemplary attaching and detaching procedure using an attachment part of a delivery member. FIG. 19*a* illustrates a view of a first step of the procedure, FIG. 19*b* illustrates a view of a second step of the procedure, FIG. 19*c* illustrates an enlargement of section 19*c* of FIG. 19*b*, and FIG. 19*d* illustrates a third step of the procedure.

Figure 20B:
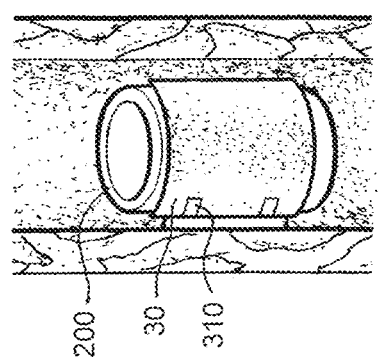
Figure 20A:
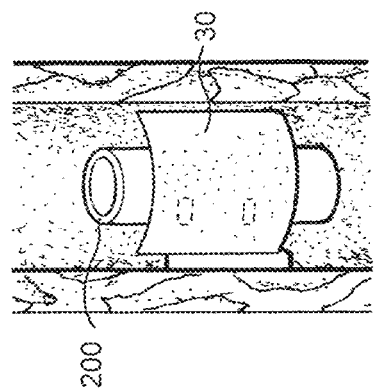

FIGS. 20*a* and 20*b* illustrate partially sectional views of an exemplary detaching procedure using an attachment part of a delivery member. FIG. 20*a* illustrates a view of a first step of the procedure, and FIG. 20*b* illustrates a view of a second step of the procedure.

FIGS. 21*a*-21*e* illustrate perspective views of an exemplary attaching and detaching procedure using an attachment part of a delivery member. FIG. 21*a* illustrates a view of a first step of the procedure, FIG. 21*b* illustrates a view of a second step of the procedure, FIG. 21*c* illustrates a view of a third step of the procedure, FIG. 21*d* illustrates a view of a fourth step of the procedure, and FIG. 21*e* illustrates a perspective view of the attachments parts used in the procedure.

FIG. 22 illustrates a longitudinal side view of an attachment part of a delivery member.

Figure 23F:
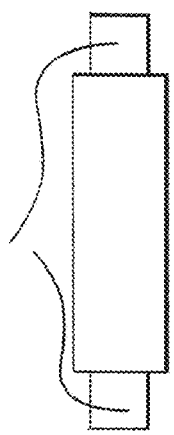
Figure 23G:
Figure 23H:
Figure 23I:
Figure 23J:
Figure 23A:
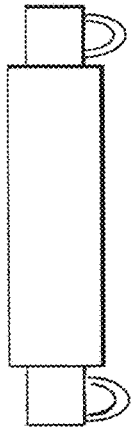
Figure 23B:
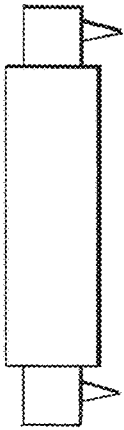
Figure 23C:
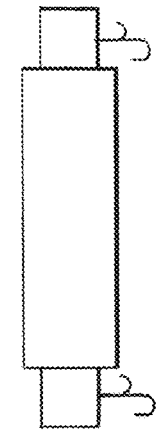
Figure 23D:
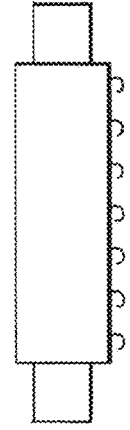
Figure 23E:
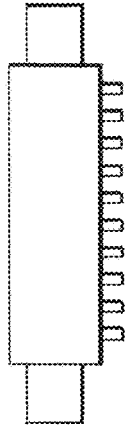

FIGS. 23*a*-23*j* illustrate longitudinal side views of alternative attachment part embodiments. FIG. 23*a* illustrates a view of a first alternative embodiment, FIG. 23*b* illustrates a view of a second alternative embodiment, FIG. 23*c* illustrates a view of a third alternative embodiment, FIG. 23*d* illustrates a view of a fourth alternative embodiment, FIG. 23*e* illustrates a view of a fifth alternative embodiment, FIG. 23*f* illustrates a view of a sixth alternative embodiment, FIG. 23*g* illustrates a view of a seventh alternative embodiment, FIG. 23*h* illustrates a view of an eighth alternative embodiment, FIG. 23*i* illustrates a view of a ninth alternative embodiment, and FIG. 23*j* illustrates a view of a tenth alternative embodiment.

Figure 24C:
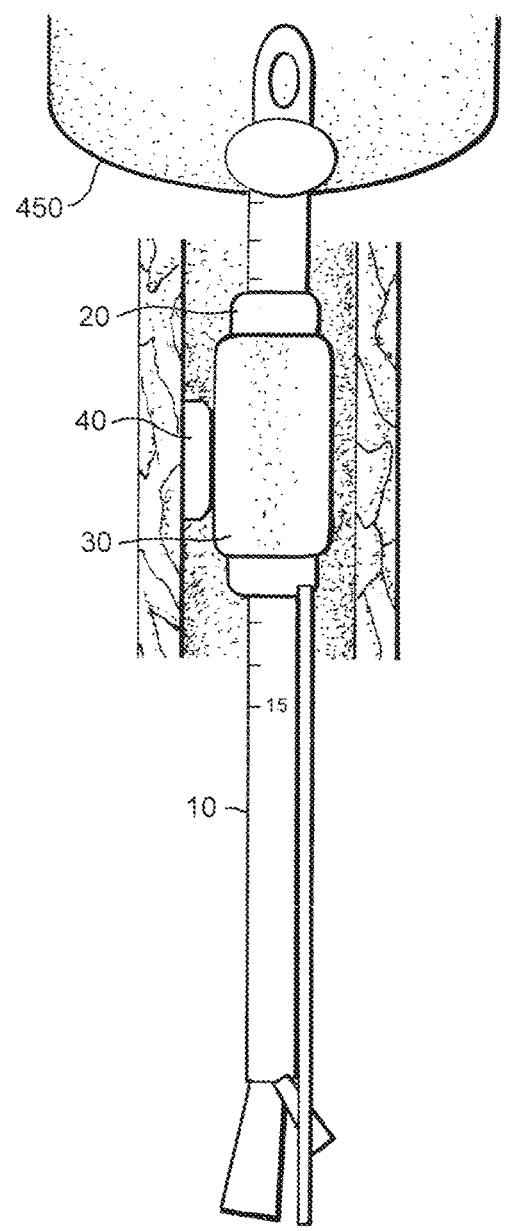

FIGS. 24*a*-24*c* illustrate partially sectional views of an exemplary method and apparatus for positioning the delivery member relative to the treatment area. FIG. 24*a* illustrates a view of a first step of the method, FIG. 24*b* illustrates a view of a second step of the method, and FIG. 24*c* illustrates a view of a third step of the method.

Figure 25A:
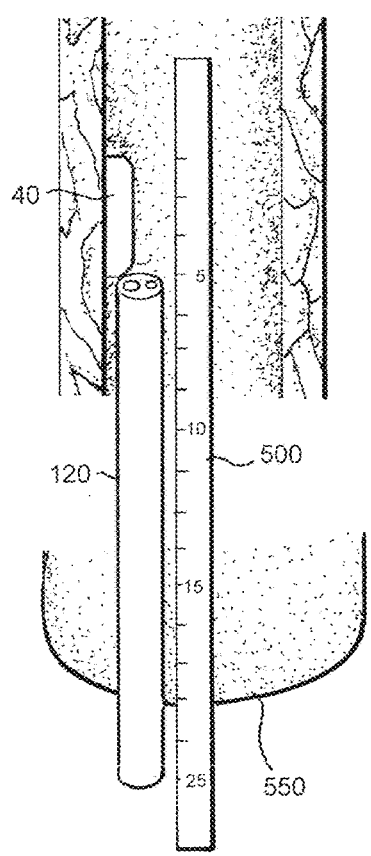
Figure 25B:
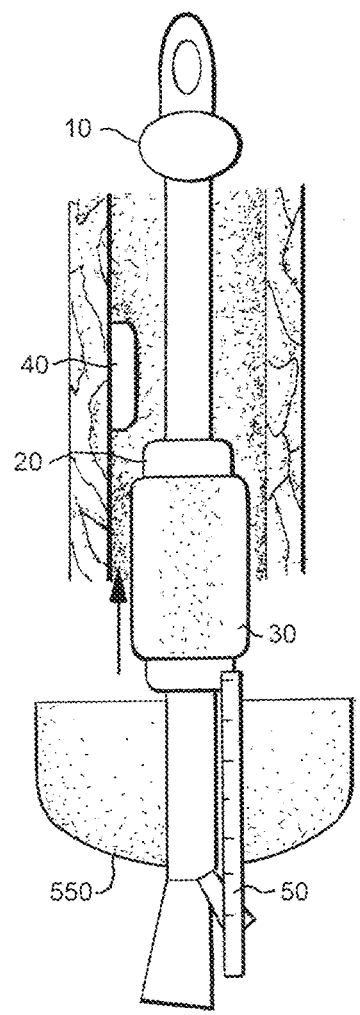
Figure 25C:
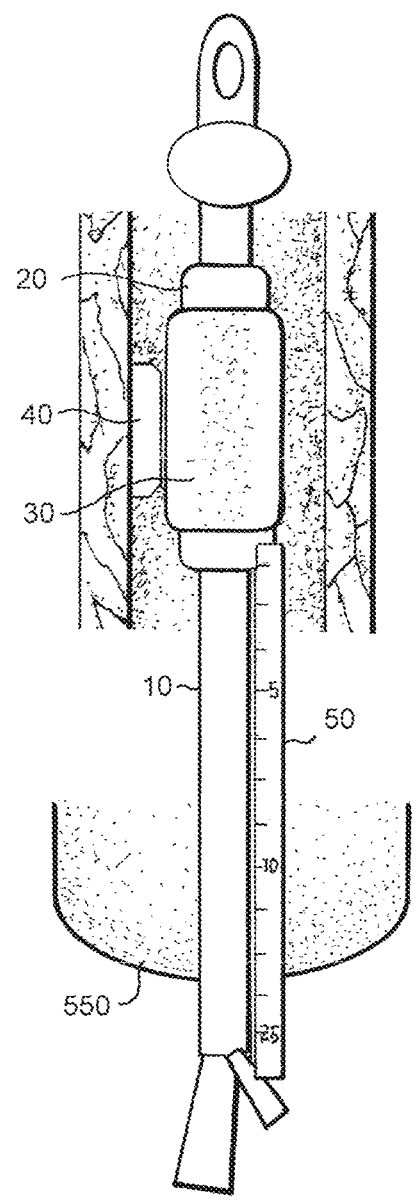

FIGS. 25*a*-25*c* illustrate partially sectional views of another exemplary method and apparatus for positioning the delivery member relative to the treatment area. FIG. 25a illustrates a view of a first step of the method, FIG. 25b illustrates a view of a second step of the method, and FIG. 25c illustrates a view of a third step of the method.

Figure 26A:
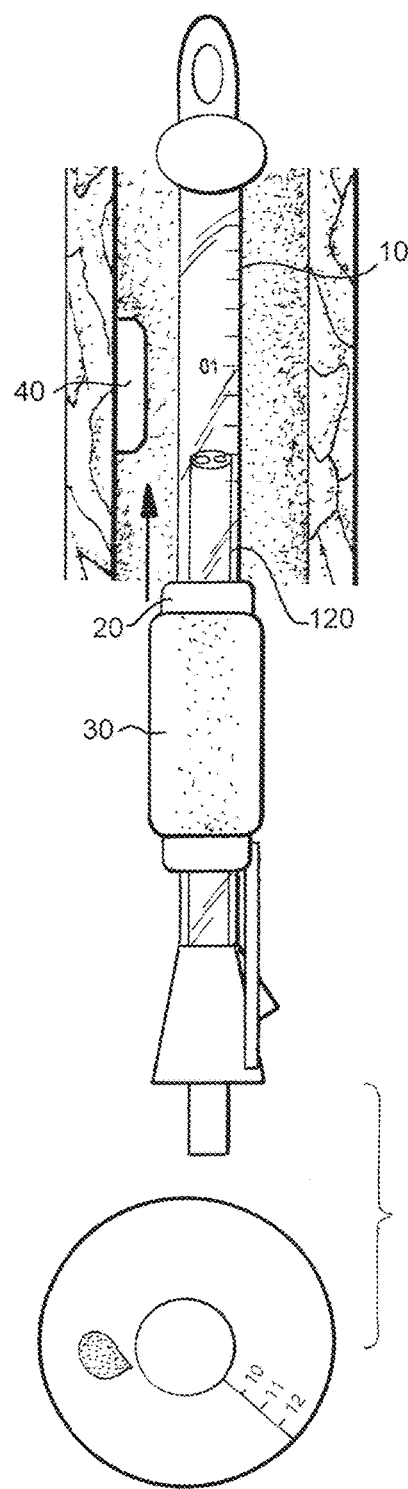
Figure 26B:
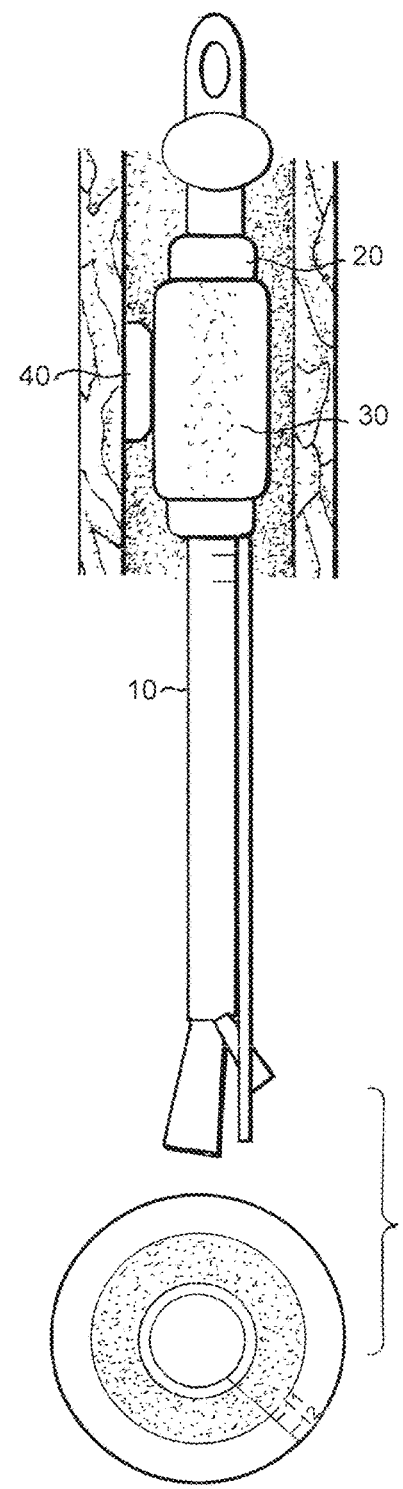

FIGS. 26a and 26b illustrate partially sectional views of another exemplary method and apparatus for positioning the delivery member relative to the treatment area. FIG. 26a illustrates a view of a first step of the method, and FIG. 26b illustrates a view of a second step of the method.

Figure 27F:
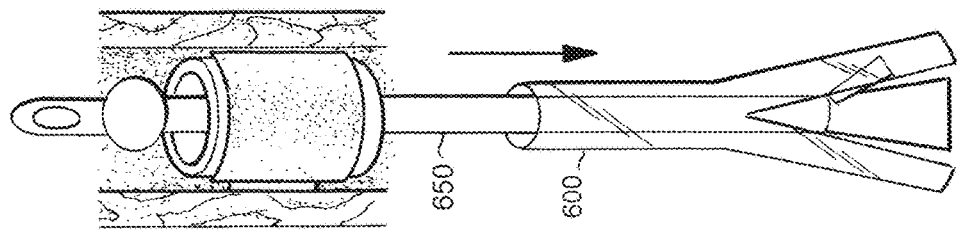
Figure 27E:
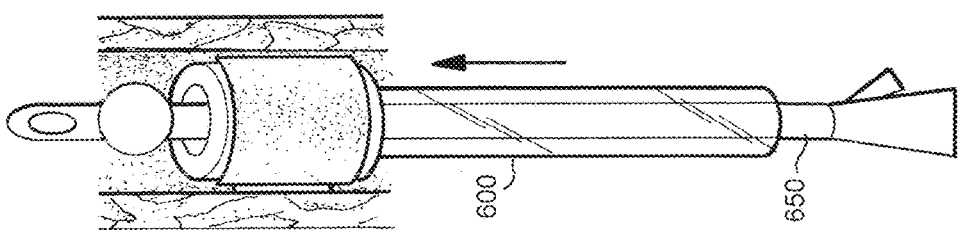
Figure 27D:
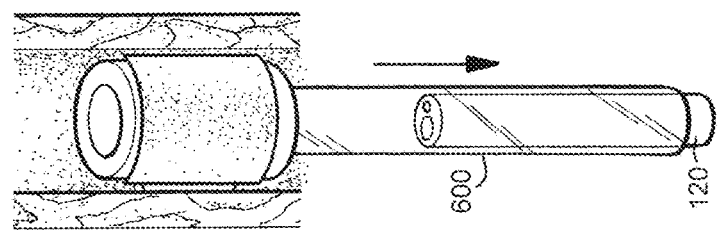
Figure 27C:
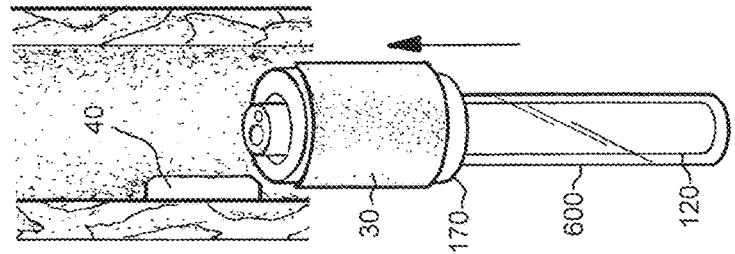
Figure 27B:
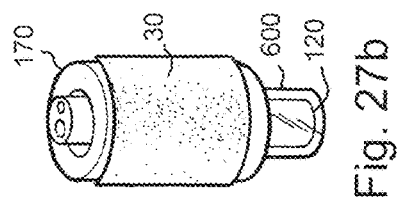
Figure 27A:
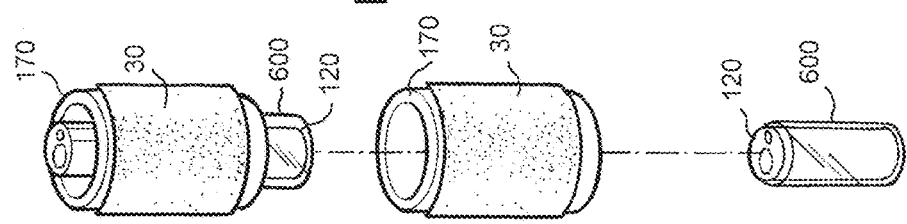

FIGS. 27a-27f illustrate partially sectional views of another exemplary method and apparatus for positioning the delivery member relative to the treatment area. FIG. 27a illustrates a view of a first step of the method, FIG. 27b illustrates a view of a second step of the method, FIG. 27c illustrates a view of a third step of the method, FIG. 27d illustrates a view of a fourth step of the method, FIG. 27e illustrates a view of a fifth step of the method, and FIG. 27f illustrates a view of a sixth step of the method.

Figures 28A, 28B:
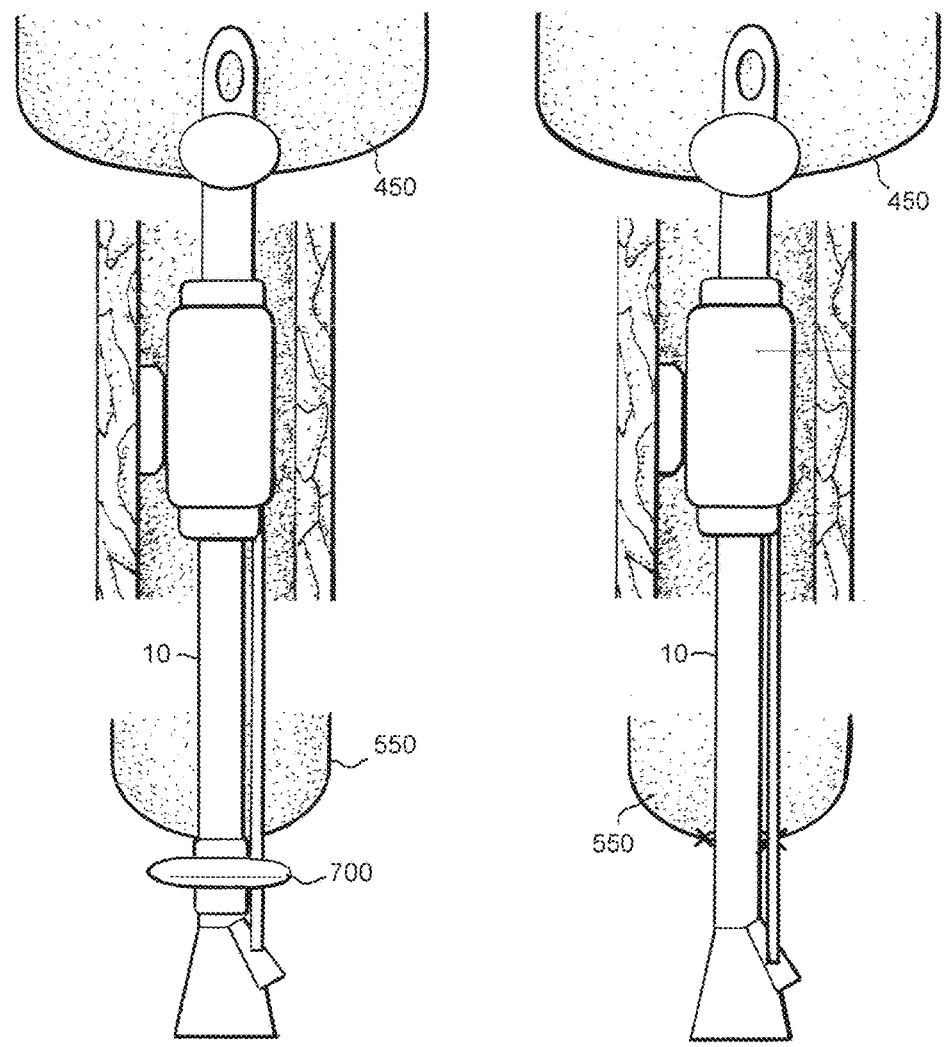

FIGS. 28a and 28b illustrate partially sectional views of exemplary methods for fixing the elongated member relative to the body lumen. FIG. 28a illustrates a view of a first step of the method, and FIG. 28b illustrates a view of a second step of the method.

Figure 29D:
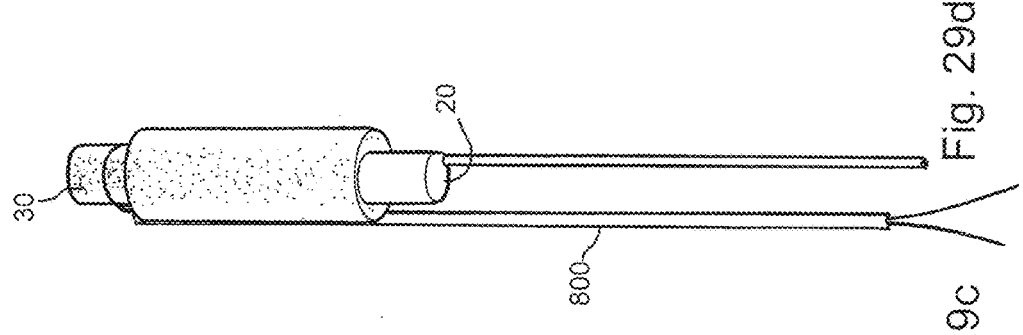
Figure 29C:
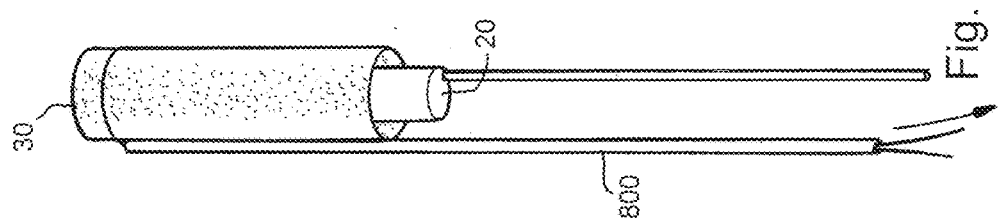
Figure 29B:
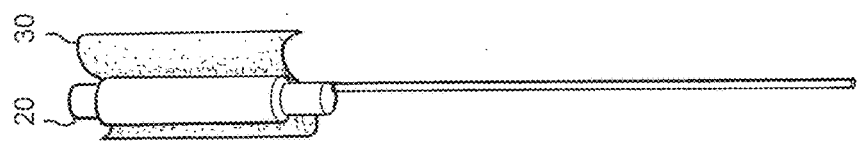
Figure 29A:
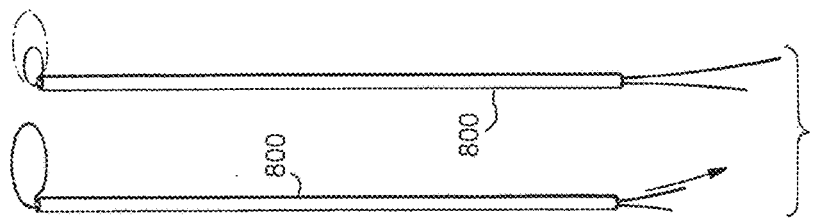
Figure 29E:
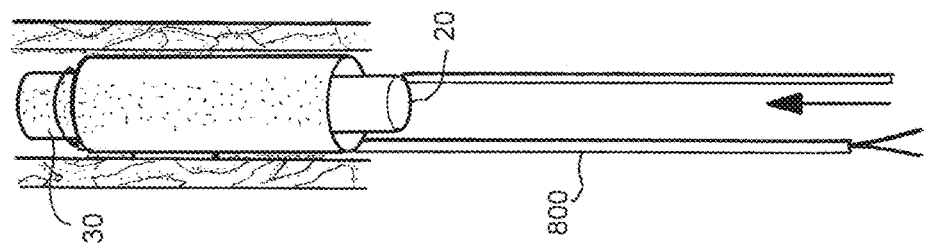
Figure 29F:
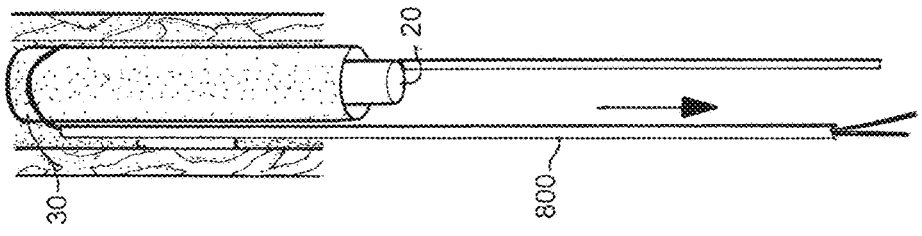
Figure 29G:
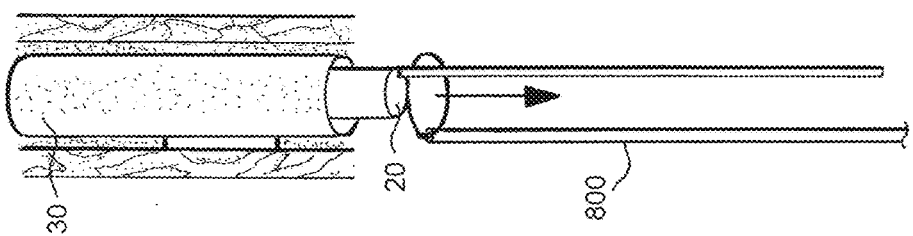
Figure 29H:
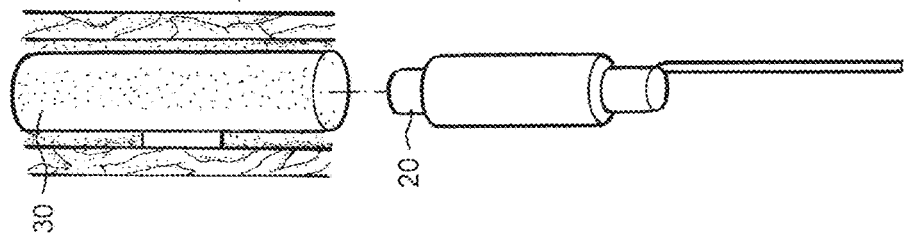

FIGS. 29a-29h illustrate partially sectional views of an exemplary method and apparatus for attaching and detaching the treatment membrane with the delivery device. FIG. 29a illustrates a view of a first step of the method, FIG. 29b illustrates a view of a second step of the method, FIG. 29c illustrates a view of a third step of the method, FIG. 29d illustrates a view of a fourth step of the method, FIG. 29e illustrates a view of a fifth step of the method, FIG. 29f illustrates a view of a sixth step of the method, FIG. 29g illustrates a view of a seventh step of the method, and FIG. 29h illustrates a view of an eighth step of the method.

Figure 30H:
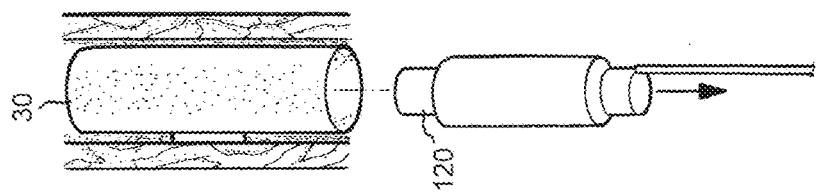
Figure 30G:
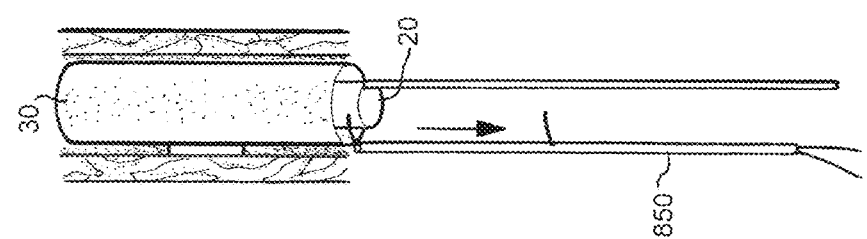
Figure 30F:
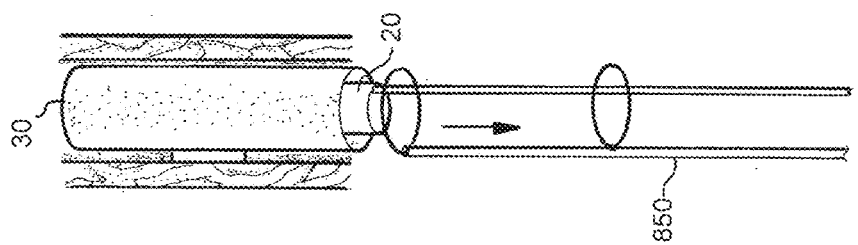
Figure 30E:
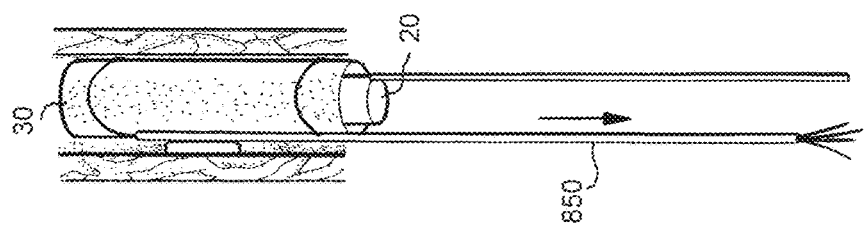
Figure 30D:
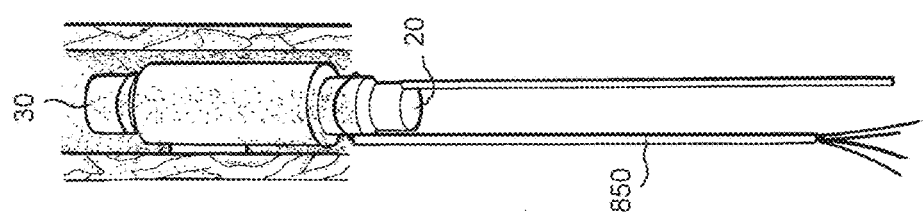

FIGS. 30a-30h illustrate partially sectional views of another exemplary method and apparatus for attaching and detaching the treatment membrane with the delivery device. FIG. 30a illustrates a view of a first step of the method, FIG. 30b illustrates a view of a second step of the method, FIG. 30c illustrates a view of a third step of the method, FIG. 30d illustrates a view of a fourth step of the method, FIG. 30e illustrates a view of a fifth step of the method, FIG. 30f illustrates a view of a sixth step of the method, FIG. 3g illustrates a view of a seventh step of the method, and FIG. 30h illustrates a view of an eighth step of the method.

FIGS. 31a-31d illustrate various views of another exemplary method and apparatus for attaching and detaching the treatment membrane with the delivery device. FIG. 31a illustrates a longitudinal side view of a first step of the method, FIG. 31b illustrates an enlargement of section 31b of FIG. 31c, FIG. 31c illustrates a longitudinal view of a second step of the method, and FIG. 31d illustrates a longitudinal side view of a third step of the method.

Figure 32A:
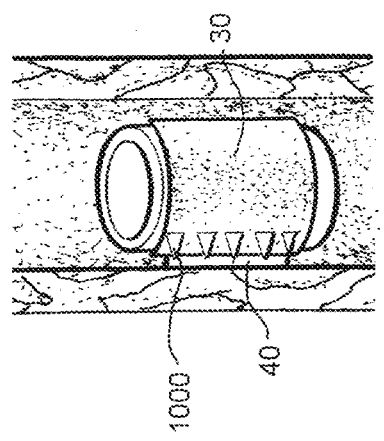
Figure 32B:
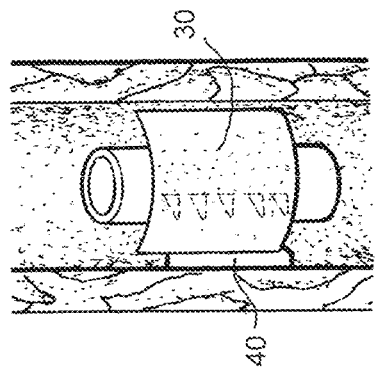
Figure 32C:
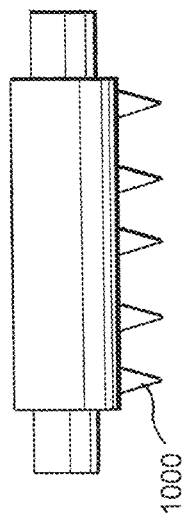

FIGS. 32a-32c illustrate various views of another exemplary method and apparatus for attaching and detaching the treatment membrane with the delivery device. FIG. 32a illustrates a partially sectional view of a first step of the method, FIG. 32b illustrates a partially sectional view of a second step of the method, and FIG. 32c illustrates a longitudinal side view of the apparatus used in the method.

DETAILED DESCRIPTION

Set forth below is a detailed description of the method and apparatus for treating urethral stricture disclosed here. The method and apparatus for treating urethral stricture is described and illustrated in terms of several embodiments disclosed as examples of the method and apparatus for treating urethral stricture.

Generally speaking, embodiments of the method involve delivering a treatment part composed of one or more of a drug, cultured cell, or harvested tissue (such as buccal mucosa from the inner cheek of the patient, preputium from the patient, or any other biocompatible sheet), to the treatment area of the body lumen, i.e., the area of urethral stricture in the patient's urethra. Prior to delivery of the treatment part to the area of the urethral stricture, the area is incised or dilated so that the recovering epithelial cell receives sufficient nutrition.

In embodiments in which the treatment part includes a drug, one or more of a collagen inhibitor such as mithramycine, mitomicyn-c, tranilast, halofuginone, or any analogs thereof, an anti-inflammatory agent such as steroids, colchicine, NSAIDs, or any analogs thereof, an anti-cancer agent such as MMC, taxotere, or any analogs thereof, an immunosuppressive agent such as sirolimus, evelolimus, zotalolimus, biolimus, or any analogs thereof, and/or a cell growth enhancing constituent such as EGF, PRP, or any analogs thereof, can be used. Furthermore, in embodiments in which the treatment part includes a biological material, cultured cell and harvested tissue from, for example, buccal mucosa, bladder mucosa, intestinal mucosa, penile skin and/or thigh skin could be selected. A form of the treatment part, which is composed of one or more of a drug/cultured cell/harvested tissue on the delivery member, could be a liquid/gel coating, powder form, film shape, or membrane form. For a membrane form, a mesh-like structure could be used.

In embodiments of this method of treating the treatment area of the body lumen, i.e., the urethra, an elongated member 10 is inserted into the urethra. In an embodiment, the elongated member 10 is an indwelling catheter, as illustrated in FIG. 1. This elongated member 10 is configured to guide a delivery member 20 which possesses an outer portion having a treatment part 30. In an embodiment, the treatment part 30 can be a drug or cultured cell coated on or covering the delivery member 20. In another embodiment the treatment part 30 is a treatment membrane, for example, of buccal mucosa harvested from the patient's inner cheek.

In an embodiment, the delivery member 20 is then moved to the treatment area 40, e.g., the area of urethral stricture in the patient's urethra. For example, in the FIG. 1 embodiment, the delivery member 20 is slid along the outer surface of the elongated member 10 until it reaches the treatment area. The delivery member 20 includes a fixing member capable of fixing the delivery member 20 to the elongated member 10. In various embodiments discussed in detail below, the fixing member is an expandable member.

Figures 2A, 2B:
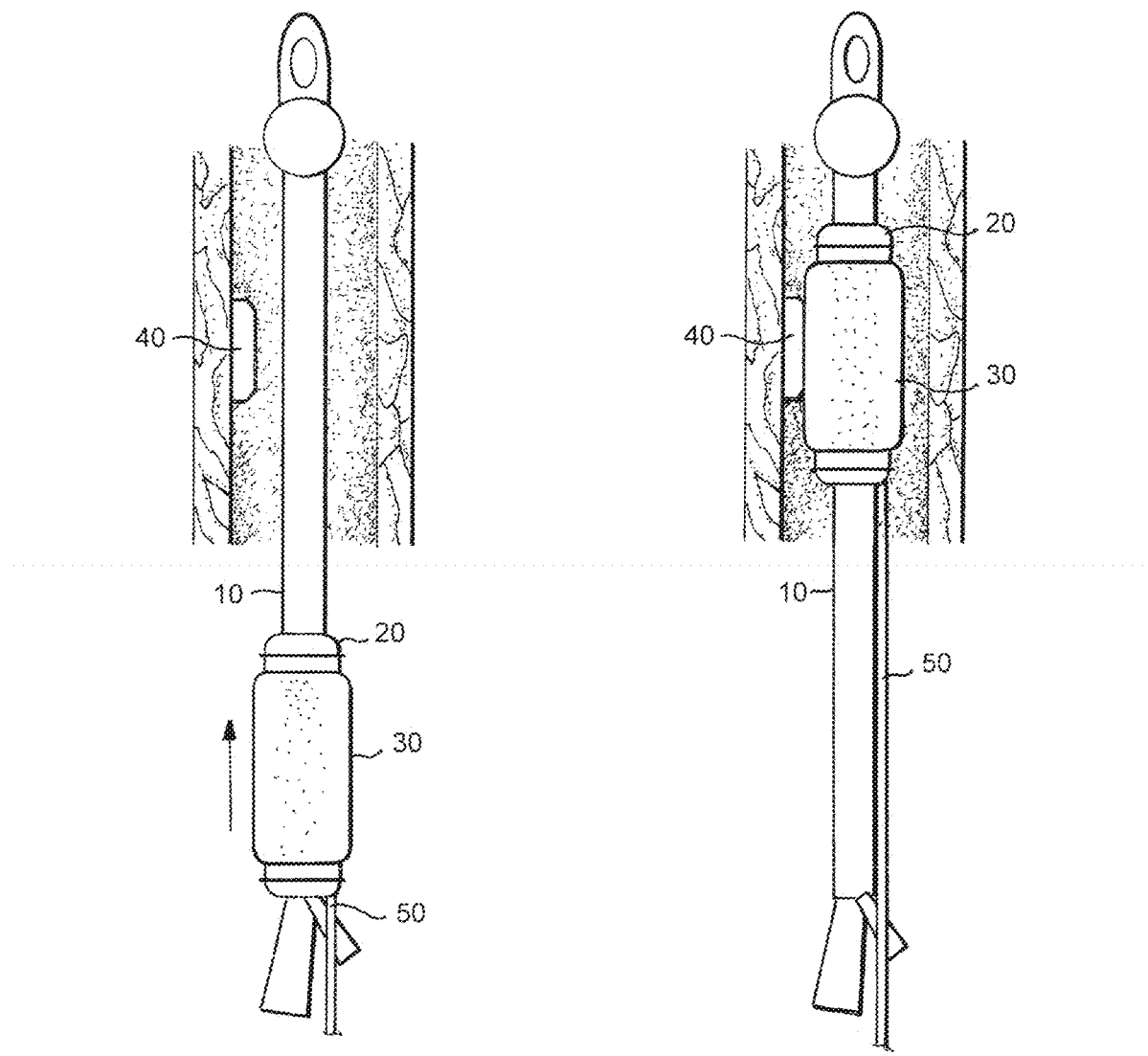
FIGS. 2a and 2b illustrate partially sectional views of an exemplary delivery procedure using the apparatus of FIG. 1.
Figures 3A, 3B, 3C:
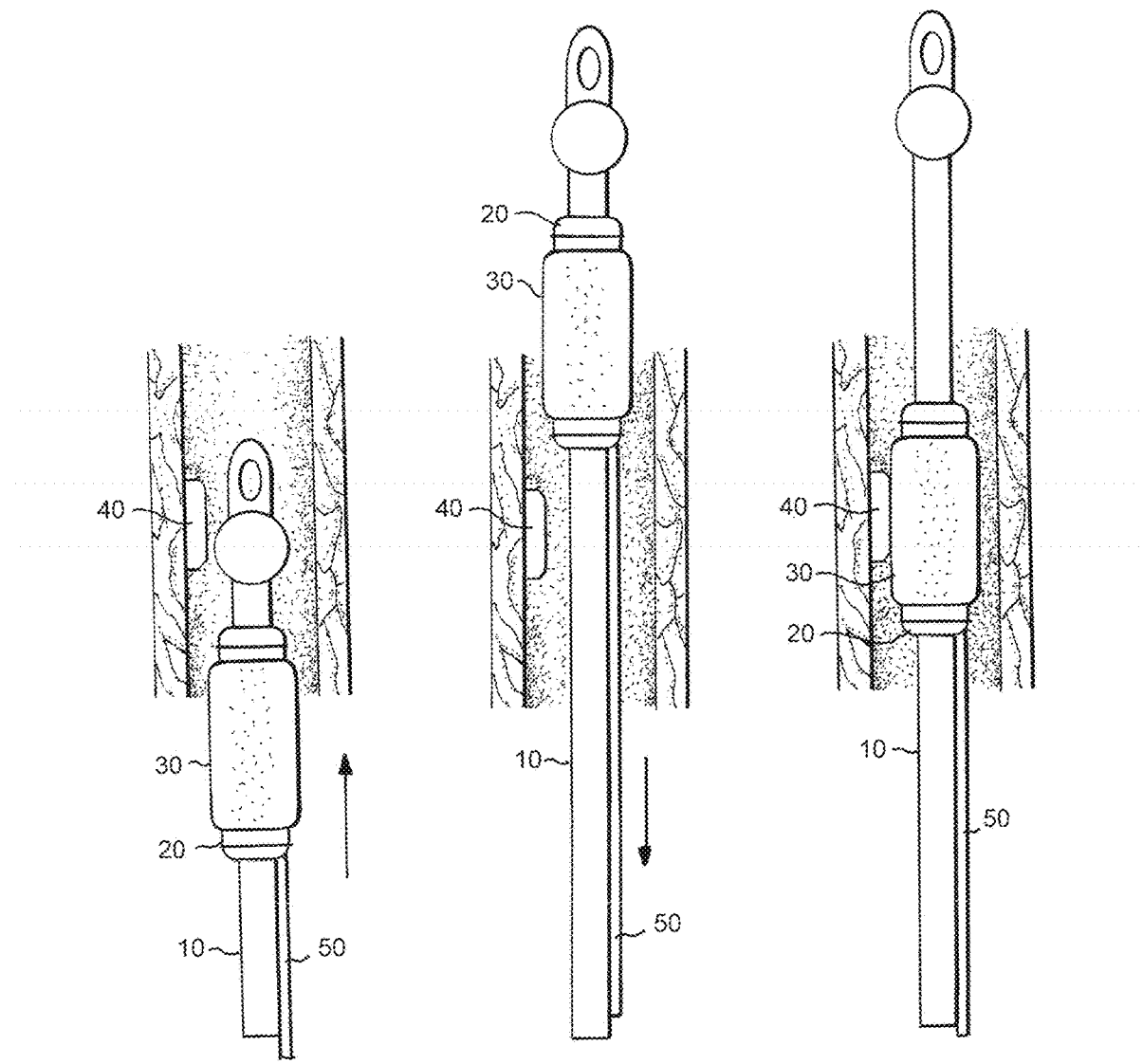
FIGS. 3a-3c illustrate partially sectional views of an exemplary delivery procedure using the apparatus of FIG. 1.

Exemplary movements of the elongated member 10 and the delivery member 20 in the insertion and moving steps are illustrated in FIGS. 2(a)-2(b) and in FIGS. 3(a)-3(c). In both procedures, in the step of inserting the elongated member 10 into the urethra, the elongated member 10 carries the delivery member 20 in an insertion direction. In the method of FIGS. 2(a)-2(b), in the step of moving the delivery member 20 to the treatment area 40, the delivery member 20 is moved in the insertion direction, while in the method of FIGS. 3(a)-3(b), in the step of moving the delivery member 20 to the treatment area 40, the delivery member 20 is moved in a direction opposite the insertion direction. Specifically, when the treatment area is located on the bulbar urethra, which lumen is narrow due to the external urethral sphincter, the operator can easily deliver the delivery member by simply pushing the delivery member toward the proximal end of the bulbar urethra. An X-ray marker can be incorporated into the delivery member 20 so that the operator can determine the position of the delivery member 20 while it is being moved. The delivery member 20 can be moved relative to the elongated member 10 by operating an operation member 50 attached to the delivery member 20. The operation member 50 can be, for example, a wire, a sheath, and/or a tube for inflating the delivery member in embodiments in which the delivery member is inflatable. The operation member 50 can be attached to the delivery member 20, or separate from the delivery member 20, in which case the operation member 50 is used as separate pusher and/or puller of the delivery member 20. In any event, the operation member 50 is configured to be operable by the operator separately from the elongated member 10, such as by having a proximal end which remains outside the urethra.

The treatment part 30 is then applied to the treatment area. In an embodiment, the outer portion of the delivery member 20 is pressed against the treatment part 30 to contact the treatment part 30 with the treatment area for a predetermined period of time. In the FIG. 1 embodiment, the delivery member 20 includes an expandable member comprising an inflatable balloon 60 which is moved to the treatment area, and the step of pressing the outer portion of the delivery member 20 against the treatment part 30 comprises expanding the expandable member by inflating the inflatable balloon 60. The expandable member can also be an inflatable sponge, or can operate by mechanical expansion, for example, in the manner of a stent.

After the predetermined period of time, the delivery member 20 is withdrawn from the treatment area. The predetermined time is a sufficient time for the treatment part 30, which is buccal mucosa in an embodiment, to graft to the treatment area due to pressure provided by the delivery member 20 and the pre-incision or pre-dilation of the treatment area by a physician.

In the FIG. 1 embodiment, the delivery member 20 includes the expandable member, and so the expandable member is moved to the treatment area at the same time the delivery member 20 is moved to the treatment area 40. When using the apparatus of this embodiment, the step of pressing the outer portion of the delivery member 20 against the treatment part 30 comprises expanding the delivery member. Additionally, in this embodiment, after the predetermined period of time, the delivery member is contracted and then the elongated member 10 is moved out of the urethra to carry the delivery member away from the treatment area and out of the urethra.

In an alternative embodiment illustrated in FIGS. 4(a)-4(c), the delivery member 20 is attached to the expandable member. In the embodiment, the delivery member 20 is a curved plate which is attached to an outer surface of the expandable member/inflatable balloon 60. Furthermore, the inflatable balloon 60 is operated and inflated through a balloon guide 70, which is, for example, a tube through which the balloon 60 can be inflated and which has a proximal end which projects out of the urethra so that it can be independently operated by the operator.

In further alternative embodiments, the apparatus can include an expandable member which is an inflatable balloon 60 separate from the delivery member 20. In this case, the expandable member/inflatable balloon 60 can be moved to the treatment area 40 before or after the delivery member 20 is moved to the treatment area 40. Additionally, in this case, to withdraw the delivery member after the predetermined period of time, the expandable member 60, which is either kept at the treatment area 40 while expanded during the predetermined time, or moved back to the treatment area 40 and expanded during or after the predetermined period of time, can be moved out of the urethra to carry the delivery member 20 away from the treatment area 40 and out of the urethra.

FIGS. 5(a)-5(d) illustrate such an embodiment in which, first, the delivery member 20 is slid along the elongated member 10 to the treatment area 40, and then the inflatable balloon 60 is slid along the elongated member 10 to the treatment area 40. The position of the inflatable balloon 60 relative to the delivery member 20 can be determined by, for example, comparing markings on the operation member 50 and the balloon guide 70 which are disposed in relative positions which line up when the delivery member 20 and the inflatable balloon 60 are at the same axial position. These markings can be, for example, X-ray markers on the operation member 50 and the delivery member 20. Alternatively, a structural positioning system, such as a stop on the delivery member 20 configured to engage with the distal end of the inflatable balloon 60 to stop further movement of the inflatable balloon 60 in the distal direction, can be provided for relative positioning of the inflatable balloon 60 relative to the delivery member 20.

In each of the embodiments which includes an expandable member such as an inflatable balloon 60, the apparatus can be configured so that, when the inflatable balloon 60 is expanded, relative sliding movement between the delivery member 20 and the elongated member 10 in the axial direction is prevented by virtue of the inflatable balloon 60 pressing on both the delivery member 20 and the elongated member 10. In each of the embodiments in which the elongated member 10 is a catheter, the catheter's lumen allows urine to pass through the urethra when the inflatable balloon 60 is expanded. Additionally, in each case, to withdraw the delivery member after the predetermined period of time, the operation member 50 is pulled to guide the delivery member 20 away from the treatment area 40 and out of the urethra.

In an alternative embodiment illustrated in FIGS. 6(a)-6(f), the delivery member possesses an inner portion 80 separate from the outer portion which presses against the treatment membrane. This inner portion 80 possesses a protrusion 90 which protrudes inwardly. The elongated member 10 possesses a groove 100 extending in an axial direction of the elongated member 10 and a plurality of spaced-apart notches 110 extend perpendicularly from the groove 100. In use, in the step of moving the delivery member to the treatment area, the protrusion 90 slides within the groove 100 in the axial direction, and after this step, the delivery member is rotated to cause the protrusion 90 to rotate into one of the plurality of notches 110, thereby preventing relative sliding movement between the delivery member and the elongated member in the axial direction. Additionally, the step of pressing the outer portion of the delivery member against the treatment membrane comprises moving the outer portion (which can have a curved plated shape such as shown in the FIG. 4 embodiment) relative to the inner portion 80 of the delivery member having the protrusion. Alternatively, the step of pressing the outer portion of the delivery member against the treatment membrane can comprise expanding an expandable member provided between the elongated member 10 and the delivery member.

FIGS. 7(a)-7(d) illustrate an embodiment in which the expandable member is moved to the treatment area after the delivery member is moved to the treatment area. In this embodiment, an endoscope 120 can be used as the elongated member to monitor the position of the delivery member 20 relative to the treatment area 40, and so in some embodiments using the endoscope 120, x-ray markings are not used. However, some embodiments use both the endoscope 120 and x-ray markings for positioning. Additionally, in this embodiment, after the step of moving the delivery member 20 to the treatment area 40, the elongated member/endoscope 120 is withdrawn from the urethra. An elongated member 10 and inflatable balloon 60 are then moved, either sequentially or simultaneously, to position the inflatable balloon relative to the delivery member 20. The inflatable balloon 60 can be fixed to the elongated member 10 such that the elongated member 10 and inflatable balloon 60 are always moved simultaneously, but this is not required The position of the inflatable balloon 60 relative to the delivery member 20 can be determined by, for example, comparing markings on the operation member 50 and the balloon guide 70 which are disposed in relative positions which line up when the delivery member 20 and the inflatable balloon 60 are at the same axial position. These markings can be, for example, X-ray markers on the operation member 50 and the delivery member 20. Alternatively, a structural positioning system, such as a stop on the delivery member 20 configured to engage with the distal end of the inflatable balloon 60 to stop further movement of the inflatable balloon 60 in the distal direction, can be provided for relative positioning of the inflatable balloon 60 relative to the delivery member 20.

The embodiment of FIGS. 8(a)-8(e) is similar to the embodiment of FIGS. 7(a)-7(d) except that the outer portion of delivery member 20 (which is a curved plate in the embodiment) faces a side of the urethra opposite the treatment area 40. This affords a clear view of the treatment area 40 by the endoscope 120. In this embodiment, after the step of moving the delivery member 20 to the treatment area 40 and before the step of pressing the outer portion of the delivery member 20 against the treatment part 30, the delivery member 20 is rotated to a position in which the outer portion of the delivery member 20 faces the treatment area 40.

In the apparatus of the embodiment of FIGS. 9(a)-9(e), a one-way expandable member 150 is used as the delivery member, with the treatment part 30 being mounted to this one-way expandable member 150. The one-way expandable member 150 has an annular inner surface that is fixed and an expandable annular outer surface. The one-way expandable member 150 is removably mounted to an expandable intermediate member 160, which is mounted to elongated member/endoscope 120. The expandable intermediate member 160 is a two-way expandable member in that it expands at both its annular inner surface and its annular outer surface.

In the method illustrated in FIGS. 9(a)-9(e), before the step of inserting the elongated member/endoscope 120 into the urethra, the delivery member/one-way expandable member 150 is mounted onto the expandable intermediate member 160 and the elongated member/endoscope 120, and the expandable intermediate member 160 is expanded to prevent relative movement between the delivery member/one-way expandable member 150 and the elongated member/endoscope 120. The elongated member 120 is then moved in the axial direction to move the delivery member 150 and intermediate member 160 to the treatment area 40. The delivery member 150 is then expanded to press the outer portion of the delivery member 150 against the treatment part 30, thereby contacting the treatment part 30 with the treatment area 40. The intermediate member 160 is then contracted, and the delivery member 150 is dismounted from the intermediate member 160 and the elongated member 120 by pulling back the elongated member 120, which still carries the intermediate member 160, thus leaving the delivery member 150 at the treatment area 40. An indwelling catheter can then be inserted into the delivery member 150 for urine drainage while the delivery member 150 is in position. After the predetermined period of time, which, as discussed above, is a sufficient time for the treatment part 30 to graft to the treatment area 40, the steps are reversed, i.e., the indwelling catheter is removed, the intermediate member 160 is moved to the treatment area 40 via the elongated member/endoscope 120 and expanded to prevent relative movement between the delivery member 150 and the elongated member 120, the delivery member 150 is contracted, and then the elongated member 120, with the intermediate member 160 and delivery member 150 mounted thereon, is removed from the urethra. An alternative process for removing the delivery member 150 involves pulling on an operation member, such as an inflation tube (not shown) attached to the delivery member 150 and used for expanding and contracting the delivery member 150.

FIGS. 10(a)-10(e) illustrate an embodiment of a method which uses a similar apparatus as the embodiment of FIG. 9(a)-9(e). However, in the method of FIGS. 10(a)-10(e), when the treatment area 40 is visible through the elongated member/endoscope 120 and before the delivery member 150 and intermediate member 160 reach the treatment area 40, the intermediate member 160 is contracted, and the delivery member 150 is dismounted from the intermediate member 160 and the elongated member 120 and moved to the treatment area 40 via the operation member 50. The delivery member 150 can be moved to the treatment area 40, with the intermediate member 160, or, in alternative embodiment, without the intermediate member 160. The delivery member 150 is then expanded to press the outer portion of the delivery member 150 against the treatment part 30, thereby contacting the treatment part 30 with the treatment area 40. As in the embodiment of FIGS. 9(a)-9(e), an indwelling catheter is inserted in the delivery member 150 and the delivery member 150 is kept in position for the predetermined period of time and removed after the predetermined period of time. The process for removing the delivery member 150 from the treatment area 40 after the predetermined period of time is the same as that described above with respect to the embodiment of FIGS. 9(a)-9(e) such as by pulling on the unillustrated inflation tube attached the delivery member 150.

In the apparatus of the embodiment of FIGS. 11(a)-11(e), a two-way expandable member 170 is used as the delivery member, with the treatment part 30 being mounted to this two-way expandable member 170. The two-way expandable member 170 expands at both its annular inner surface and its annular outer surface. The two-way expandable member 170 is removably mounted to the elongated member/endoscope 120.

In the method illustrated in FIGS. 11(a)-11(e), before the step of inserting the elongated member/endoscope 120 into the urethra, the delivery member/two-way expandable member 170 is mounted onto the elongated member/endoscope 120, and the delivery member/two-way expandable member 170 is expanded to prevent relative movement between the delivery member/two-way expandable member 170 and the elongated member/endoscope 120. The elongated member 120 is then moved in the axial direction to move delivery member/two-way expandable member 170 to the treatment area 40. The delivery member/two-way expandable member 170 is then contracted to allow relative movement between the delivery member/two-way expandable member 170. The delivery member/two-way expandable member 170 is then pulled back, resulting in dismounting of the delivery member/two-way expandable member 170 from the elongated member/endoscope 120, and then the delivery member/two-way expandable member 170 is again expanded to press the outer portion of the delivery member/two-way expandable member 170 against the treatment part 30, thereby contacting the treatment part 30 with the treatment area 40. An indwelling catheter is then inserted into the delivery member/two-way expandable member 170. After the predetermined period of time, which, as discussed above, is a sufficient time for the treatment part 30 to graft to the treatment area 40, the steps are reversed, i.e., the indwelling catheter is removed, the delivery member/two-way expandable member 170 is contracted, the endoscope/elongated member is then reintroduced into the delivery member/two-way expandable member 170 and the delivery member/two-way expandable member 170 re-expanded, and then the elongated member/endoscope 120, with the delivery member/two-way expandable member 170 mounted thereon, is removed from the urethra. In the embodiment, the delivery member/two-way expandable member 170 may be removed by pulling on the unillustrated inflation tube attached to the delivery member/two-way expandable member.

The method illustrated in FIGS. 12(a)-12(e) is similar to that illustrated in FIGS. 11(a)-11(e) except that the delivery member is a one-way expandable member 180 having a fixed outer surface, i.e., only the inner surface changes size to be able to mount to and dismount from the endoscope 120. The method of use is the same as that illustrated in FIGS. 11(a)-11(e) except that the delivery member/one-way expandable member 180 is not re-expanded after removal of the elongated member/endoscope 120 until after the elongated member/endoscope 120 has been reinserted into the delivery member/one-way expandable member 180 for removal of the delivery member/one-way expandable member 180, or at all in the case in which the delivery member/one-way expandable member 180 is removed by pulling on an unillustrated inflation tube attached to the delivery member/one-way expandable member 180. In this embodiment, the delivery member/one-way expandable member 180 is large enough outer diameter for successful engraftment of the treatment part 30 to the treatment area 40.

In embodiments in which the delivery member is an expandable member having an adjustable outer circumference, i.e., an expandable outer surface, the treatment part 30 may be an expandable treatment membrane. In such embodiment, in order to mount the treatment part 30 to the delivery member/expandable member 200, the treatment part 30 is wrapped around the expandable member 200, the opposite overlapped edges of the expandable member 200 are pinched, and then the opposite overlapped edges of the expandable member 200 are attached together by, for example, suturing or heat sealing. FIGS. 13(a)-13(b) illustrate an exemplary process in which the pinching of the opposite overlapped edges of the treatment part 30 together is done with a clip part 220 of a clip device 210. Alternatively, the treatment part 30 can first be wrapped around a mold and the opposite overlapped edges attached together, then the mold is removed, then the treatment part 30 mounted to the expandable member 200.

The circumference of the treatment part 30 can be set by setting the circumference of the expandable member 200 to be the desired circumference of the treatment part 30. And by using a clip device 210 which includes an indicator 230, such as a ruler which provides an indication of a size of the expandable member 200, as illustrated in FIGS. 14(a)-14(b), the expandable member 200 can be expanded during the mounting process based on the indication. Furthermore, by using a clip device 210 which also includes a limiter 240 which limits the size of the expandable member 200, as illustrated in FIGS. 15(a)-15(b), expansion of the expandable member 200 can be automatically stopped based on a setting of the limiter 240.

As illustrated in FIGS. 16(a)-16(b), the clip device 210 can further include a cavity 250, in which case the method will further include positioning the treatment part 30 and the expandable member 200 in the cavity and, if necessary, expanding the expandable member 200 while the treatment part 30 and the expandable member 200 are positioned in the cavity 250. In an embodiment, a plurality of clip devices 210 having different sized cavities can be made available, and the circumference of the treatment part 30 can be set by selecting the clip device 200 having the appropriately-sized cavity.

The clip device 210 illustrated in FIGS. 16(a)-16(b) also possesses suturing holes 260 configured to align with the opposite overlapped edges of the treatment part 30. When such suturing holes 260 are provided, the opposite overlapped edges of the treatment part 30 can be attached by performing a suturing operation through the suturing holes 260. The clip device 210 illustrated in FIGS. 16(a)-16(b) further possesses suturing holes 270 configured to align with opposite ends of the treatment part 30. When such suturing holes 270 are provided, the opposite ends of the treatment part 30 can be at least partially closed by performing a suturing operation through the suturing holes 270. In more detail, as shown in the FIG. 16c view of the bottom of the clip device 210, one suturing hole 270 is provided at each end of the bottom, while as shown in the FIG. 16d view of the bottom of the clip device 210, two suturing holes are provided at each end of the top. A suture passing through the suturing holes 270 of one end of the clip device 210 can tighten that end of the treatment part 30 around that end of the expandable member 200. Since, as illustrated in FIG. 13(a), the expandable member 200 can have smaller-circumference ends serving as attachment parts, tightening each end of the treatment part 30 around the smaller-circumference ends of the expandable member 200 can serve to immobilize the treatment part 30 with respect to the expandable member 200. The treatment part 30 can then be released from the expandable member 200 at the appropriate time of the procedure by pulling on the strings which are used to provide the sutures through the suturing holes 270.

In the clip devices 210 described above, the clip part 220 of the clip device 210 possesses two opposed clip portions which are forced together by a spring force. With this configuration, the step of pinching the opposite overlapped edges of the treatment part 30 with the clip part 220 comprises providing a force which opposes the spring force to move the opposed clip portions apart, moving the opposite overlapped edges of the treatment part 30 to a pinching operation position, and releasing the force which opposes the spring force to allow the spring force to force the opposed clip portions together at the pinching operation position to thereby pinch the opposite overlapped edges.

In an alternative embodiment, a clip device, such as the clip device 280 illustrated in FIGS. 17(a)-17(c), can be provided, in which the clip part comprises completely separable opposed clip portions 290. With such a clip device 280, the step of pinching the opposite overlapped edges of the treatment part 30 with the clip part comprises separating the opposed clip portions 290, moving the opposite overlapped edges of the treatment part 30 to a pinching operation position, and bringing the opposed clip portions 290 together at the pinching operation position to thereby pinch the opposite overlapped edges. Furthermore, the circumference of the treatment part 30 can be selected by selecting opposed clip portions 290 with the appropriately sized cavity portions 300. A spring mechanism can also be used in this embodiment to assist in bringing the opposed clip portions 290 together.

The delivery member can also include attachment parts to assist in attaching and detaching the treatment part 30, which can be a treatment membrane, to and from the delivery device. In the embodiment illustrated in FIGS. 18(*a*)-18(*b*), the delivery member/expandable member 200 includes an attachment part 310 at each end, and the opposite edges of the treatment part 30 are sutured directly to the attachment parts 310. FIGS. 19(*a*)-19(*d*) illustrate a similar embodiment in which the treatment part 30 is attached to each attachment part 320 by virtue of suturing opposite edges of the treatment part 30 such that openings are defined through which the attachment parts 320 protrude. The curved shape of the attachment parts 320 assists in keeping the treatment part 30 attached even though it is not directly sutured to the attachment parts 320 in this embodiment. In these embodiments, the delivery member 200 and attached treatment part 30 can be considered to together constitute a therapeutic device.

As illustrated in FIG. 19(*d*), in the embodiment in which curved attachment parts 320 are used, the delivery member 200 be rotated to cause the curved attachment parts to 320 retract through the openings defined by the sutures and thereby detach the treatment part 30 from the delivery member 200. The delivery member 200 can then be withdrawn from the urethra. Furthermore, in embodiments in which the delivery member 200 is an expandable member, the expandable member can additionally or alternatively be contracted in the detachment process, as illustrated in FIGS. 20(*a*) and 20(*b*).

FIGS. 21(*a*)-21(*c*) illustrate a further embodiment in which each attachment part 330 is formed as two oppositely curved portions, and the treatment part 30 is detached by rotating the delivery member 200 in first one direction, and then the other direction.

FIG. 22 illustrates an alternative embodiment in which the attachment parts comprise slits 340 in the delivery member 200. Such slits 340 can be configured to engage portions of the treatment part 30 or sutures in the treatment part 30, and can detach from such portions by rotating the delivery member 200.

Further alternative embodiments of attachment parts include tabs for suturing opposite ends of the treatment part 30 thereto illustrated in FIG. 23(*a*), tips for piercing opposite ends of the treatment part 30 as illustrated in FIG. 23(*b*), hooks for hooking across the treatment part 30 as illustrated in FIGS. 23(*c*) and 23(*d*), and straight attachment parts, such as those illustrated in FIGS. (18*a*) and (18*b*) but provided across the treatment part 30 as illustrated in FIG. 23(*e*). Additionally, the attachment parts can be strings for binding opposite ends of the treatment part 30 as illustrated in FIGS. 23(*f*) and 23(*g*), suction cups for suctioning opposite ends of the treatment part 30 as illustrated in FIG. 23(*h*), adhesive sheets for adhering to opposite ends of the treatment part 30 as illustrated in FIG. 23(*i*), and suction holes for suctioning across the treatment part 30 as illustrated in FIG. 23(*j*). The various attachment parts can be located on opposite ends of the treatment part 30, across the treatment part 30, or both.

Various methods for ensuring that the delivery member is provided at the delivery area are discussed above. Additional methods which can be adapted to the previously discussed embodiments are illustrated in FIGS. 24-28.

In the method illustrated in FIGS. 24(*a*)-24(*c*), prior to insertion of the elongated member and delivery member into the urethra, a measuring member 400, such as a wire or tube with a blunt distal end and measurement markings starting from the distal end, is inserted into the urethra until its distal end reaches the subject's bladder neck 450 (as determined by resistance of the measuring member 400 to further insertion). An endoscope 120 is then used to view the measurement markings next to the treatment area 40. Such measurement markings can be used to determine the length between the bladder neck 450 and the treatment area 40. Next, the delivery member 20 is fixed to the elongated member 10 at an appropriate position based on the known length from the bladder neck 450 to the treatment area 40 which would cause the treatment part 30 to line up with the treatment area 40 when the blunt distal portion of the elongated member 10 reaches the bladder neck 450. Measurement markings can be provided on the elongated member 10 for positioning of the delivery member 20 relative to the elongated member 10.

In the method illustrated in FIGS. 25(*a*)-25(*c*), prior to insertion of the elongated member and delivery member into the urethra, a measuring member 500, such as a wire or tube or sheath with measurement markings starting from the distal end, is inserted into the urethra until its distal end reaches the treatment area 40, as determined by an endoscope 120. The operator can then use the measurement markings on the measuring member 500 to visually determine the length from the treatment area to the external urethra meatus 550. With this information, the operator can more precisely position the delivery member 20 and treatment part 30. For example, in an embodiment in which the elongated member 10 is inserted into the urethra, and then the delivery member 20 moved along the elongated member 10, measurement markings on the operation member 50 can be used to determine that the delivery member 20 has moved within the urethra the same length as the length between the treatment area 40 and the external urethra meatus 550. In this case, the delivery member 20 will have been moved to the treatment area 40. The operator can also determine the length between the treatment area and another anatomical landmark. The anatomical landmark includes, for example, the bladder neck, the external urethra meatus, or the membranous urethra.

After these steps, the delivery member 20 is fixed to the elongated member 10 to avoid unexpected movement of the treatment membrane mounted on the delivery member from the treatment area 40 during the predetermined period of time.

The proper positioning of the delivery member 20 can also be monitored by using a clear indwelling catheter for the elongated member 10 and providing an endoscope 120 within the clear indwelling catheter so that the operator can visually determine that the delivery member 20 has been provided at the treatment area. Alternatively, as illustrated in FIGS. 26(*a*)-26(*c*), a clear indwelling catheter having measurement markings starting from the blunt distal end can be used as the elongated member 10. In this method, the distance between the bladder neck and the treatment area 40 is first measured, for example, in the manner described with respect to FIG. 24(*a*). Then, the endoscope 120 can be provided within the inserted elongated member 120 to view the position of the delivery member relative to the measurement markings on the elongated member 120 to help with proper positioning of the delivery member 20 relative to the treatment area 40.

Another type of clear elongated member that can be used as a delivery member is a clear sheath 600, as illustrated in FIGS. 27(a)-27(f). The method in this embodiment is similar to the method used in FIGS. 11(a)-11(f) except that, instead of being mounted directly to the endoscope 120, the delivery member 170 is mounted to the clear sheath 600, and the endoscope 120 is positioned within the clear sheath 600 to view the position of the delivery member 170 relative to the treatment area 40. When the endoscope 120 is withdrawn, the clear sheath 600 remains. After the indwelling catheter 650 is inserted into the clear sheath 600 and the delivery member 170, the clear sheath 600 is withdrawn.

FIGS. 28(a) and 28(b) illustrate methods for fixing the position of the elongated body/indwelling catheter 10 relative to the treatment area 40. In FIG. 28(a), a stopper 700 is fixed to the appropriate position on the elongated body/ indwelling catheter 10 to engage with the external urethra meatus. In more general terms, the elongated body 10 is fixed to at least one side of the edge of the body lumen. This can also be accomplished by suturing the external urethra meatus to the side of the elongated body 10, as illustrated in FIG. 28(b). Additionally or alternatively, the distal end of the elongated body/indwelling catheter 10 can be fixed relative to the bladder neck 450 by, for example, hooking or hanging. Fixation of the delivery member 20 to the elongated body/ indwelling catheter 10 further ensure to avoid unexpected movement of the treatment membrane mounted on the delivery member from the treatment area 40 during the predetermined period of time.

FIGS. 29(a)-29(h) and 30(a)-30(h) illustrate alternative methods of attaching and detaching the treatment part 30 with the delivery member 20 using a snare device. In FIGS. 29(a)-29(h), the snare device 800 is a string extending back and forth through a pipe and looped at one end. Pushing and pulling the string at the other end of the pipe increases and decreases the size of the loop. In the illustrated embodiment, the loop is provided around the distal end of the treatment membrane and pulled tight to contract that end of the treatment membrane around one of the smaller-circumference ends of the delivery member (the distal end in the embodiment). At the appropriate time, the loop is expanded to detach the treatment part 30 from the delivery member 20. In the method of FIGS. 30(a)-30(h), a snare device 850 having two loops to snare both smaller-diameter ends of the delivery member 20 is used. In this embodiment, as an alternative to expanding the loops to detach the treatment part 30 from the delivery member 20, the loops can instead be cut.

Alternatively, as illustrated in FIGS. 31(a)-31(c), snare loops 900 can be formed by providing openings 950 in the smaller-circumference ends of the delivery member 20 and running strings through the respective sets of openings 950. By pulling both strings for a particular loop, that loop can be tightened to attached the treatment part 30 to the delivery member 20. At the appropriate time, a single string for each loop can be pulled to remove the strings entirely and allow the treatment part 30 to detach from the delivery member.

As a further alternative, one or more puncturing members 1000 can be provided on the delivery member 20, as shown in FIGS. 32(a)-32(c). When the delivery member 20 is expanded, the puncturing devices 1000 puncture the treatment membrane to attached the treatment part 30 to the delivery member 20. The puncturing devices 1000 can also be configured to puncture the wall of the urethra. In this embodiment, in order to detach the treatment part 30, the delivery member 20 is contracted to pull the puncture devices 1000 out of the treatment part 30 and/or the wall of the urethra.

The detailed description above describes features and aspects of embodiments of a trans-urethral urethroplasty method and apparatus disclosed by way of example. The invention is not limited, however, to the precise embodiments and variations described. Changes, modifications and equivalents can be employed by one skilled in the art without departing from the spirit and scope of the invention as defined in the appended claims. It is expressly intended that all such changes, modifications and equivalents which fall within the scope of the claims are embraced by the claims.

What is claimed is:

1. A method of treating a treatment area of a body lumen, the treatment area comprising a urethral stricture, the method comprising:
   inserting an elongated member into the body lumen, wherein said elongated member is an endoscope configured to guide a delivery member, said delivery member possessing an outer surface on which is mounted a treatment part comprising a buccal mucosa;
   moving the delivery member to the urethral stricture by sliding the delivery member in its entirety along the endoscope;
   contacting the treatment part with the urethral stricture for a predetermined period of time while the treatment part remains mounted on the outer surface of the delivery member; and
   withdrawing the delivery member from the urethral stricture after the predetermined period of time.

2. The method of claim 1, wherein the delivery member possesses a fixing member capable of fixing the delivery member to the elongated member.

3. The method of claim 2, further comprising fixing the delivery member to the elongated member via the fixing member after moving the delivery member to the urethral stricture.

4. The method of claim 2, further comprising fixing the delivery member to the elongated member via the fixing member before moving the delivery member to the urethral stricture.

5. The method of claim 2, further comprising unfixing the delivery member from the elongated member via the fixing member and withdrawing the elongated member from the delivery member.

6. The method of claim 2, wherein the fixing member comprises an expandable member.

7. The method of claim 6, wherein the expandable member comprises an inflatable balloon.

8. The method of claim 7, wherein the inflatable balloon possesses an inner portion and an outer portion, the delivery member is fixed to the elongated member by inflating the inner portion, and the treatment part is contacted with the urethral stricture by inflating the outer portion.

9. The method of claim 1, wherein the delivery member comprises an expandable member, and contact with the urethral stricture is maintained by inflating the expandable member.

10. The method of claim 9, wherein the expandable member comprises an inflatable balloon.

11. The method of claim 1, further comprising, after the step of inserting the elongated member into the body lumen, fixing the elongated member to at least one side of the edge of the body lumen.

12. The method of claim 1, further comprising, before the step of withdrawing the delivery member from the urethral stricture, detaching the treatment part from the delivery member.

13. The method of claim 1, further comprising, after the step of moving the delivery member to the urethral stricture, rotating the delivery member to a position in which the treatment part faces the urethral stricture.

14. The method of claim 1, further comprising contracting the delivery member to allow relative movement between the delivery member and the elongated member and then dismounting the delivery member from the elongated member.

15. The method of claim 1, further comprising, before the step of inserting the elongated member into the body lumen, measuring the length between an anatomical landmark and the urethral stricture.

16. The method of claim 15, wherein the anatomical landmark includes the bladder neck, the external urethra meatus, or the membranous urethra.

17. The method of claim 1, wherein, in the step of moving the delivery member to the urethral stricture, the delivery member is delivered under endoscopic view.

18. The method of claim 1, wherein, in the step of moving the delivery member to the urethral stricture, the delivery member is slid along an outer surface of the elongated member.

19. A method of treating a treatment area of a body lumen, the treatment area comprising a urethral stricture, the method comprising:

inserting an elongated member into the body lumen, wherein said elongated member is an endoscope configured to guide a delivery member, said delivery member possessing an outer surface on which is mounted a treatment part comprising a buccal mucosa;

moving the delivery member to the urethral stricture by sliding the delivery member in its entirety along the endoscope;

applying the treatment part to the urethral stricture while the treatment part remains mounted on the outer surface of the delivery member; and withdrawing the delivery member from the urethral stricture.

20. The method of claim 19, wherein the delivery member possesses a fixing member capable of fixing the delivery member to the elongated member.

21. The method of claim 19, further comprising moving the delivery member to the urethral stricture by sliding the delivery member along an outer surface of the elongated member.

* * * * *